United States Patent
Carvalho et al.

(10) Patent No.: US 7,476,733 B2
(45) Date of Patent: Jan. 13, 2009

(54) DEVELOPMENT OF A REAL-TIME PCR ASSAY FOR DETECTION OF PNEUMOCOCCAL DNA AND DIAGNOSIS OF PNEUMOCOCCCAL DISEASE

(75) Inventors: Maria da Gloria Carvalho, Decatur, GA (US); Jacquelyn S. Sampson, College Park, GA (US); Edwin W. Ades, Atlanta, GA (US); George Carlone, Stone Mountain, GA (US); Karen McCaustland, Snellville, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/089,938

(22) Filed: Mar. 25, 2005

(65) Prior Publication Data
US 2006/0216720 A1 Sep. 28, 2006

(51) Int. Cl.
C07H 21/04 (2006.01)
(52) U.S. Cl. .................... 536/24.3; 536/24.32
(58) Field of Classification Search .............. None
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman et al. |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis et al. |
| 4,948,882 A | 8/1990 | Ruth et al. |
| 4,958,013 A | 9/1990 | Letsinger et al. |
| 4,981,957 A | 1/1991 | Lebleu et al. |
| 5,023,243 A | 6/1991 | Tullis et al. |
| 5,034,506 A | 7/1991 | Summerton et al. |
| 5,082,830 A | 1/1992 | Brakel et al. |
| 5,109,124 A | 4/1992 | Ramahandran et al. |
| 5,112,963 A | 5/1992 | Pieles et al. |
| 5,118,800 A | 6/1992 | Smith et al. |
| 5,118,802 A | 6/1992 | Smith et al. |
| 5,124,136 A | 6/1992 | Davis et al. |
| 5,130,302 A | 7/1992 | Spielvogel et al. |
| 5,134,066 A | 7/1992 | Rogers et al. |
| 5,135,917 A | 8/1992 | Burch et al. |
| 5,138,045 A | 8/1992 | Cook et al. |
| 5,166,315 A | 11/1992 | Summerton et al. |
| 5,168,053 A | 12/1992 | Atlman et al. |
| 5,175,273 A | 12/1992 | Bischofberger et al. |
| 5,176,996 A | 1/1993 | Hogan et al. |
| 5,177,196 A | 1/1993 | Meyer, Jr. et al. |
| 5,185,444 A | 2/1993 | Summerton et al. |
| 5,188,897 A | 2/1993 | Suhaadolnik et al. |
| 5,214,134 A | 5/1993 | Weis et al. |
| 5,216,141 A | 6/1993 | Benner et al. |
| 5,218,105 A | 6/1993 | Cook et al. |
| 5,235,033 A | 8/1993 | Summerton et al. |
| 5,245,022 A | 9/1993 | Weis et al. |
| 5,252,465 A | 10/1993 | Nigon et al. |
| 5,252,711 A | 10/1993 | Rogers et al. |
| 5,254,469 A | 10/1993 | Warren, III et al. |
| 5,258,506 A | 11/1993 | Urdea et al. |
| 5,262,536 A | 11/1993 | Hobbs et al. |
| 5,264,423 A | 11/1993 | Cohen et al. |
| 5,264,562 A | 11/1993 | Matteucci et al. |
| 5,264,564 A | 11/1993 | Matteucci et al. |
| 5,272,873 A | 12/1993 | Hamazaki et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,294,533 A | 3/1994 | Lupski et al. |

(Continued)

FOREIGN PATENT DOCUMENTS

WO    WO 92/03566    3/1992

(Continued)

OTHER PUBLICATIONS

Berry et al. Sequence heterogeneity of PsaA, a 37-kilodalton putative adhesin essential for virulence of *Streptococcus pneumoniae*. Infection and Immunity (1996) 64:5255-5262.*

(Continued)

*Primary Examiner*—Kenneth R. Horlick
*Assistant Examiner*—David C Thomas
(74) *Attorney, Agent, or Firm*—Klarquist Sparkman, LLP.

(57) ABSTRACT

Disclosed are compositions and methods for detecting a specific sequence of the psaA gene using real-time PCR for diagnosis of Pneumococcal Disease.

19 Claims, 5 Drawing Sheets

U.S. PATENT DOCUMENTS

| | | |
|---|---|---|
| 5,317,098 A | 5/1994 | Shizuya et al. |
| 5,319,080 A | 6/1994 | Leumann et al. |
| 5,321,131 A | 6/1994 | Agrawal et al. |
| 5,334,711 A | 8/1994 | Sproat et al. |
| 5,359,044 A | 10/1994 | Cook et al. |
| 5,367,066 A | 11/1994 | Urdea et al. |
| 5,371,241 A | 12/1994 | Brush et al. |
| 5,391,878 A | 2/1995 | Petroff et al. |
| 5,393,878 A | 2/1995 | Leumann et al. |
| 5,399,676 A | 3/1995 | Froehler et al. |
| 5,405,938 A | 4/1995 | Summerton et al. |
| 5,405,939 A | 4/1995 | Suhadolink et al. |
| 5,414,077 A | 5/1995 | Lin et al. |
| 5,416,203 A | 5/1995 | Letsinger et al. |
| 5,432,272 A | 7/1995 | Benner et al. |
| 5,434,257 A | 7/1995 | Matteucci et al. |
| 5,436,330 A | 7/1995 | Taira et al. |
| 5,443,137 A | 8/1995 | Welser et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,766 A | 12/1995 | Gold et al. |
| 5,476,925 A | 12/1995 | Letsinger et al. |
| 5,484,908 A | 1/1996 | Froehler et al. |
| 5,486,603 A | 1/1996 | Buhr et al. |
| 5,489,677 A | 2/1996 | Sanghvi et al. |
| 5,502,177 A | 3/1996 | Matteucci et al. |
| 5,503,978 A | 4/1996 | Schneider et al. |
| 5,510,475 A | 4/1996 | Agrawal et al. |
| 5,512,667 A | 4/1996 | Reed et al. |
| 5,514,785 A | 5/1996 | Van Ness et al. |
| 5,519,126 A | 5/1996 | Hecht et al. |
| 5,519,134 A | 5/1996 | Acevedo et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth et al. |
| 5,543,293 A | 8/1996 | Gold et al. |
| 5,545,730 A | 8/1996 | Urdea et al. |
| 5,550,111 A | 8/1996 | Suhadolink et al. |
| 5,552,538 A | 9/1996 | Urdea et al. |
| 5,552,540 A | 9/1996 | Haralambidis et al. |
| 5,561,225 A | 10/1996 | Maddy et al. |
| 5,562,426 A | 10/1996 | Watanabe et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,718 A | 11/1996 | Cook et al. |
| 5,580,731 A | 12/1996 | Chang et al. |
| 5,580,737 A | 12/1996 | Polisky et al. |
| 5,580,967 A | 12/1996 | Joyce et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,873 A | 1/1997 | Joyce et al. |
| 5,596,091 A | 1/1997 | Switzer et al. |
| 5,597,086 A | 1/1997 | King-Shui |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Sessler et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,616,466 A | 4/1997 | Cantor et al. |
| 5,618,704 A | 4/1997 | Sangnvi et al. |
| 5,623,070 A | 4/1997 | Cook et al. |
| 5,624,824 A | 4/1997 | Yuan et al. |
| 5,625,050 A | 4/1997 | Beaton et al. |
| 5,627,053 A | 5/1997 | Usman et al. |
| 5,627,158 A | 5/1997 | Cho-Chung et al. |
| 5,631,115 A | 5/1997 | Ohtsuka et al. |
| 5,631,146 A | 5/1997 | Szostak et al. |
| 5,633,133 A | 5/1997 | Long et al. |
| 5,633,360 A | 5/1997 | Biscofberger et al. |
| 5,639,873 A | 6/1997 | Barascut et al. |
| 5,641,754 A | 6/1997 | Iversen et al. |
| 5,645,985 A | 7/1997 | Froehler et al. |
| 5,646,020 A | 7/1997 | Swiggen et al. |
| 5,646,031 A | 7/1997 | DeYoung et al. |
| 5,646,042 A | 7/1997 | Stinchcomb et al. |
| 5,646,265 A | 7/1997 | McGee et al. |
| 5,650,316 A | 7/1997 | Aggarwal et al. |
| 5,652,094 A | 7/1997 | Usman et al. |
| 5,652,107 A | 7/1997 | Lizardi et al. |
| 5,658,873 A | 8/1997 | Bertsch-Frank et al. |
| 5,663,200 A | 9/1997 | Bhagwat et al. |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,683,873 A | 11/1997 | George et al. |
| 5,683,874 A | 11/1997 | Kool et al. |
| 5,683,902 A | 11/1997 | Hampel et al. |
| 5,688,670 A | 11/1997 | Szostak et al. |
| 5,688,941 A | 11/1997 | Cook et al. |
| 5,691,317 A | 11/1997 | Cho-Chung et al. |
| 5,693,535 A | 12/1997 | Draper et al. |
| 5,693,773 A | 12/1997 | Kandimalla et al. |
| 5,700,920 A | 12/1997 | Altnmann et al. |
| 5,712,384 A | 1/1998 | Symonds et al. |
| 5,714,331 A | 2/1998 | Buchard et al. |
| 5,728,521 A | 3/1998 | Yuan et al. |
| 5,731,424 A | 3/1998 | Toothman et al. |
| 5,770,715 A | 6/1998 | Sugiyama et al. |
| 5,780,228 A | 7/1998 | Parama et al. |
| 5,780,607 A | 7/1998 | Goodnow, Jr. et al. |
| 5,786,138 A | 7/1998 | Swenson et al. |
| 5,786,462 A | 7/1998 | Schneider et al. |
| 5,792,613 A | 8/1998 | Schmidt et al. |
| 5,795,721 A | 8/1998 | Rabin et al. |
| 5,807,718 A | 9/1998 | Joyce et al. |
| 5,811,300 A | 9/1998 | Sullivan et al. |
| 5,834,185 A | 11/1998 | Ts'o et al. |
| 5,837,855 A | 11/1998 | Chowrira et al. |
| 5,846,026 A | 12/1998 | Gilbert et al. |
| 5,846,713 A | 12/1998 | Pagratis et al. |
| 5,849,903 A | 12/1998 | Pietrzkowski et al. |
| 5,854,416 A | 12/1998 | Sampson et al. |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schneider et al. |
| 5,861,288 A | 1/1999 | Usman et al. |
| 5,866,701 A | 2/1999 | Hampel et al. |
| 5,869,246 A | 2/1999 | Matsuo et al. |

| | | | |
|---|---|---|---|
| 5,869,253 | A | 2/1999 | Draper et al. |
| 5,869,339 | A | 2/1999 | Hampel et al. |
| 5,869,641 | A | 2/1999 | Jayasena et al. |
| 5,874,566 | A | 2/1999 | Veerapanane et al. |
| 5,877,021 | A | 3/1999 | Stinchcomb et al. |
| 5,877,022 | A | 3/1999 | Stinchcomb et al. |
| 5,877,162 | A | 3/1999 | Werner et al. |
| 5,891,683 | A | 4/1999 | Usman et al. |
| 5,891,684 | A | 4/1999 | Usman et al. |
| 5,910,408 | A | 6/1999 | Szostak et al. |
| 5,919,772 | A | 7/1999 | Szyf et al. |
| 5,955,590 | A | 9/1999 | Levina et al. |
| 5,958,691 | A | 9/1999 | Pieken et al. |
| 5,972,699 | A | 10/1999 | Draper et al. |
| 5,972,704 | A | 10/1999 | Draper et al. |
| 5,985,621 | A | 11/1999 | Usman et al. |
| 5,989,906 | A | 11/1999 | Thompson et al. |
| 5,989,908 | A | 11/1999 | Scanlon et al. |
| 5,990,088 | A | 11/1999 | Ensol et al. |
| 5,994,320 | A | 11/1999 | Low et al. |
| 5,998,193 | A | 12/1999 | Keese et al. |
| 5,998,203 | A | 12/1999 | Matulic-Adamic et al. |
| 5,998,602 | A | 12/1999 | Torrence et al. |
| 6,001,988 | A | 12/1999 | Parma et al. |
| 6,005,095 | A | 12/1999 | Capaccioli et al. |
| 6,007,995 | A | 12/1999 | Baker et al. |
| 6,011,020 | A | 1/2000 | Gold et al. |
| 6,013,443 | A | 1/2000 | Heilig et al. |
| 6,013,522 | A | 1/2000 | Monia et al. |
| 6,017,756 | A | 1/2000 | Draper et al. |
| 6,017,898 | A | 1/2000 | Pietrzkowski et al. |
| 6,018,042 | A | 1/2000 | Mett et al. |
| 6,020,130 | A | 2/2000 | Gold et al. |
| 6,022,962 | A | 2/2000 | Chowrira et al. |
| 6,025,198 | A | 2/2000 | Bennett et al. |
| 6,028,186 | A | 2/2000 | Tasset et al. |
| 6,030,776 | A | 2/2000 | Easton et al. |
| 6,033,910 | A | 3/2000 | Monia et al. |
| 6,040,296 | A | 3/2000 | Nyce et al. |
| 6,046,004 | A | 4/2000 | Wu et al. |
| 6,046,319 | A | 4/2000 | Power et al. |
| 6,051,698 | A | 4/2000 | Janjic et al. |
| 6,057,437 | A | 5/2000 | Kamiya et al. |
| 6,573,082 | B1 | 6/2003 | Choi et al. |

FOREIGN PATENT DOCUMENTS

| | | |
|---|---|---|
| WO | WO 93/22434 | 11/1993 |
| WO | WO 95/24489 | 9/1995 |
| WO | WO 97/18312 | 5/1997 |
| WO | WO 98/58057 | 12/1998 |
| WO | WO 98/58058 | 12/1998 |
| WO | WO 00/77254 | 12/2000 |
| WO | WO 01/00233 | 1/2001 |
| WO | WO 2004/090159 | 10/2004 |

OTHER PUBLICATIONS

Berry et al. Sequence heterogeneity of PsaA, a 37-kilodalton putative adhesin essential for virulence of *Streptococcus pneumoniae*. GenBank Accession No. U40786 (1998).*
Greiner et al. Quantitative detection of *Streptococcus pneumoniae* in nasopharyngeal secretions by real-time PCR. J. Clin. Microbiol. (2001) 39:3129-3134.*
Buck et al. Design strategies and performance of custom DNA sequencing primers. BioTechniques (1999) 27:528-536.*
Alizadeh, M., Bernard, M., Danic, B., Dauriac, C., Birebent, B., Lapart, C., Lamy, T., Le Prise, P.Y., Beauplet. A., Bories, D., Semana, G & Quelvennec, E. (2002) Quantitative assessment of hematopoietic chimerism after bone marrow transplantation by real-time quantitative polymerase chain reaction. *Blood*, 99, 4618-4625.
Bernard, P.S., Ajioka, R.S., Kushner, J.P. & Wittwer. C.T. (1998) Homogeneous multiplex genotyping of hemochromatosis mutations with fluorescent hybridization probes. *Am J Pathol*, 153, 1055-1061.

Berry, A. M., R. A. Lock, D. Hansman, and J. C. Paton. (1989.) Contribution of autolysin to virulence of *Streptococcus pneumoniae*. Infect. Immun. 57: 2324-2330.
Bischoff, F.Z., Sinacori, M.K., Dang, D.D., Marquez-Do, D., Horne, C., Lewis, D.E. & Simpson, J.L. (2002) Cell-free fetal DNA and intact fetal cells in maternal blood circulation: implications for first and second trimester non-invasive prenatal diagnosis. *Hum Reprod Update*, 8, 493-500.
Bremer, C., Tung, C.H. & Weissleder, R. (200) Molecular imaging of MMP expression and therapeutic MMP inhibition. *Acad Radiol*, 9 Suppl 2, S314-315.
Brennan, R.E. & Samuel, J.E. (2003) Evaluation of *Coxiella burnetii* antibiotic susceptibilities by real-time PCR assay. *J Clin Microbiol* 41, 1869-1874.
Brown, P. D., and S. A. Lerner. (1998.) Community-acquired pneumonia. Lancet 352:1295-1302.
Bryant, P.A., Li, H.Y., Zaia, A., Griffith, J., Hogg, G., Curtis, N. & Carapetis, J.R. (2004) Prospective study of a real-time PCR that is highly sensitive, specific, and clinically useful for diagnosis of meningococcal disease in children. *J Clin Microbiol*, 42, 2919-2925.
Burger, H., Foekens, J.A., Look, M.P., Meijer-van Gelder, M.E., Klijn, J.G., Wiemer, E.A., Stoter, G. & Nooter, K. (2003) RNA expression of breast cancer resistance protein, lung resistance-related protein, multidrug resistance-associated proteins 1 and 2, and multidrug resistance gene 1 in breast cancer: correlation with chemotherapeutic response. *Clin Cancer Res*, 9, 827-836.
Bustin, S.A. (2000) Absolute quantificatiion of mRNA using real-time reverse transcription polymerase chain reaction assays. *J Mol Endocrinol*, 25, 169-193.
Bustin, S.A. (2002) Quantificatiion of mRNA using real-time reverse transcription PCR (RT-PCR): trends and problems. *J Mol Endocrinol*, 29, 23-39.
Chen. X., Zehnbauer, B., Gnirke, A. & Kwok, P.Y. (1997) Fluorescence energy transfer detection as homogeneous DNA diagnostic method. *Proc Natl Acad Sci U S A*, 94, 10756-10761.
Cherian, T., M. K. Lalitha, A. Manoharan, K. Thomas, R. H. Yolken, and M. C. Steinhoff. (1998.) PCR-enzyme immunoassay for detection of *Streptococcus pneumoniae* DNA in cerebrospinal fluid samples from patients with culture-negative meningitis. J. Clin. Microbiol. 36:3605-3608.
Cilloni, D., Gottardi, E., De Micheli, D., Serra, A., Volpe, G., Messa, F., Rege-Cambrin, G., Guerrasio, A., Divona, M., Lo Coco, F. & Saglio, G. (2002) Quantitative assessment of WT1 expression by real-time quantitative PCR may be a useful tool for monitoring minimal residual disease in actue leukemia patients. *Leukemia*, 16, 2115-2121.
Cleary, T.J., Roudel, G., Casillas, O. & Miller, N. (2003) Rapid and specific detection of Mycobacterium tuberculosis by using the Smart Cycler instrument and a specific fluorogenic probe. *J Clin Microbiol*, 41, 4783-4786.
Cottrell, S.E., Distler. J., Goodman, N.S., Mooney, S.H., Kluth, A., Olek, A., Schwope, I., Tetzner, R., Ziebarth, H. & Berlin, K. (2004) A real-time PCR assay for DNA-methylation using methylation-specific blockers. *Nucleic Acids Res*, 32, e10.
Coupry, I., Monnet, L., Attia, A.A., Taine, L., Lacombe, D. & Areviler, B. (2004) Analysis of CBP (CREBBP) gene deletions in Rubinstein-Taybi syndrome patients using real-time quantitative PCR. *Hum Mutat*, 23, 278-284.
Covault, J., Abreu, C., Kranzler, H. & Oncken, C. (2003) Quantitative real-time PCR for gene dosage determinations in microdeletion genotypes. *Biotechniques*, 35, 594-596, 598.
de Kok, J.B., Roelofs, R.W., Giesendorf, B.A., Pennings, J.L., Waas, E.T., Feuth, T., Swinkels, D.W. & Span, P.N. (2004) Normalization of gene expression measurements in tumor tissues: comparison of 13 endogenous control genes. *Lab Invest*.
Dheda, K., Huggett, J.F., Bustin, S.A., Johnson, M.A., Rook, G & Zumla, A. (2004) Validation of housekeeping genes for normalizing RNA expression in real-time PCR. *Biotechniques*, 37, 112-114, 118-119.
Dietmaier, W. & Hofstadter, F. (2001) Detection of microsatellite instability by real time PCR and hybridization probe melting point analysis. *Lab Invest*, 81, 1453-1456.

Doern, G. V., A. B. Brueggemann, H. Huynh, and E. Wingert. (1999.) Antimicrobial resistance with *Streptococcus pneumoniae* in the United States, 1997-98. Emerg. Infect. Dis. 5:757-765.

Donohoe, G.G., Laaksonen, M., Pulkki, K., Ronnemaa, T. & Kairisto, V. (2000) Rapid single-tube screening of the C282Y hemochromatosis mutation by real-time multiplex allele-specific PCR without fluorescent probes. *Clin Chem*, 46, 1540-1547.

du Plessis, M., A. M. Smith, and K. P. Klugman. (1999.) Application of *pbp1A* PCR in identification of penicillin-resistant *Streptococcus pneumoniae*. J. Clin Microbiol. 37:628-632.

du Plessis, M., A. M. Smith, and K. P. Klugman. (1998.) Rapid detection of penicillin-reistant *Streptococcus pneumoniae* in cerebrospinal fluid by a seminested-PCR strategy. J. Clin. Microbiol. 36:453-457.

Elmaagacli, A.H. (2002) Real-time PCR for monitoring minimal residual disease and chimerism in patients after allogeneic transplantation. *Int J Hematol*, 76 Suppl 2, 204-205.

Foulds, I. V., Granacki, A., Xiao, C., Krull, U.J., Castle, A. & Horgen, P.A. (2002) Quantification of microcystin-producing cyanobacteria and *E. coli* in water by 5'-nuclease PCR. *J Appl Microbiol*, 93, 825-834.

Freeman, W.M., Walker, S.J. & Vrana, K.E. (1999) Quantitative RT-PCR: pitfalls and potential. *Biotechniques*, 26, 112-122, 124-115.

Gabert, J., Beillard, E., van der Velden, V.H., Bi, W., Grimwade, D., Pallisgaard, N., Barbany, G., Cazzaniga, G., Cayuela, J.M., Cave, H., Pane, F., Aerts, J.L., De Micheli, D., Thirion, X., Pradel, V., Gonzalez, M., Viehmann, S., Malec, M., Saglio, G & van Dongen, J.J. (2003) Standardization and quality control studies of 'real-time' quantitative reverse transcriptase polymerase chain reaction of fusion gene transcripts for residual disease detection in leukemia—a Europe Against Cancer program. *Leukemia*, 17, 2318-2357.

Garcia, A., B. Roson, J. L. Perez, R. Verdaguer, J. Dorca, J. Carratala, A. Casanova, F. Manresa, and R. Gudiol. (1999.) Usefulness of PCR and antigen latex agglutination test samples obtained by transthoracic needle aspiration for diagnosis of pneumococcal pneumonia. J. Clin. Microbiol. 37:709-714.

Gibbs, P.J., Tan, L.C. Sadek, S.A. & Howell, W.M. (2003) Comparative evaluation of 'TaqMan' RT-PCR and RT-PCR ELISA for immunological monitoring of renal transplant recipients. *Transpl Immunol*, 11, 65-72.

Gibellini, D., Vitone, F., Gori, E., La Placa, M. & Re, M.C. (2004) Quantitative detection of human immunodeficiency virus type 1 (HIV-1) viral load by SYBR green real-time RT-PCR technique in HIV-1 seropositive patients. *J Virol Methods*, 115, 183-189.

Gillespie, S. H. (1999.) The role of molecular laboratory in the investigation of *Streptococcus pneumoniae* infections. Semin. Respiratory Infect. 14: 269-275.

Gillespie, S. H., T. D. McHugh, H. Ayres, A. Dickens, A. Efstratiou, and G. C. Whiting. (1997.) Allelic variation in *Streptococcus pneumoniae* autolysin (Nacetyl muramoyl-L-alanine amidase). Infect. Immun. 65:3936-3938.

Gillespie, S. H., C. Ullman, M. D. Smith, and V. Emery. (1994.) Detection of *Streptococcus pneumoniae* in sputum samples by PCR. J. Clin. Microbiol. 32:1308-1311.

Ginzinger, D.G., Godfrey, T.E., Nigro, J., Moore, D.H., 2nd, Suzuki, S., Pallavicini, M.G., Gray, J.W. & Jensen, R.H. (2000) Measurement of DNA copy number at microsatellite loci using quantitative PCR analysis. *Cancer Res*. 60, 5405-5409.

Grace, M.B., McLeland, C.B., Gagliardi, S.J., Smith, J.M., Jackson, W.E., 3rd & Blakely, W.F. (2003) Development and assessment of a quantitative reverse transcription-PCR assay for simultaneous measurement of four amplicons. *Clin Chem*, 49, 1467-1475.

Guy, R.A., Payment, P., Krull, U.J. & Horgen, P.A. (2003) Real-time PCR for quantification of *Giardia* and *Cryptosporidum* in environmental water sample and sewage. Appl Environ Microbiol, 69, 5178-5185.

Hall, L. M. C. 1998. Application of molecular typing the epidemiology of *Streptococcus pneumoniae*. J. Clin. Pathol. 51:270-274.

Harries, L.W., Wickham, C.L., Evans, J.C., Rule, A., Joyner, M.V. & Ellard, S. (2004) Analysis of haematopoietic chimaerism by quantitative real-time polymerase chain reaction. Bone Marrow Transplant, (in press).

Hassan-King, M., I. Baldeh, O. Secka, A. Falade, and B. Greenwood. 1994. Detection of *Streptococcus pneumoniae* DNA in blood cultures by PCR. J. Clin. Microbiol. 32:1721-1724.

Hazbon, M.H. & Alland, D. (2004) Hairpin primers for simplified single-nucleotide polymorphism analysis of Mycobacterium tuberculosis and other organisms. J Clin Microbiol, 42, 1236-1242.

He, L., Chinnerry, P.F., Durham, S.E., Blakely, E.L., Wardell, T.M., Borthwick, G.M., Taylor, R.W. & Turnbull, D.M. (2002) Detection and quantification of mitochondrial DNA deletions in individual cells by real-time PCR. Nucleic Acids Res, 30, e68.

Hendolin, P. H., A. Markkanen, J. Ylikoski, and J. J. Wahlfors. 1997. Use of multiplex PCR for simultaneous detection of four bacterial species in middle ear effusions. J. Clin. Microbiol. 35:2854-2858.

Higuchi, R. 1989. Simple and rapid preparation of samples for PCR, p. 31-38. *In* H. A. Erlich (ed.), PCR technology: principles and application for DNA amplification. Stockton Press, New York, N.Y.

Holland, P.M., Abramson, R.D., Watson, R. & Gelfand, D.H. (1991) Detection of specific polymerase chain reaction product by utilizing the 5'—3' exonuclease activity of *Thermus aquaticus* DNA polymerase. *Proc Natl Acad Sci U S A*, 88, 7276-7280.

Irwin, M. H., R. J. Moffatt, and C. A. Pinkert. 1999. Identification of transgenic mice by PCR analysis of saliva. Nat. Biotechnol. 14:1146-1148.

Isaacman, D. J., Y. Zhang, E. A. Reynolds, and G. D. Ehrlich. 1998. Accuracy of a polymerase chain reaction-based assay for detection of pneumococcal bacteremia in children. Pediatrics 101:813-816.

Jacoby, G. A. 1996. Antimicrobial-resistant pathogens in the 1990s. Annu. Rev. Med. 47:169-179.

Kawamura, Y., R. A. Whiley, S. E. Shu, T. Ezaki, and J. M. Hardie. 1999. Genetic approaches to the identification of the *mitis* group within the genus *Streptococcus*. Microbiology 145:2605-2613.

Kearns, A.M., Graham, C., Burdess, D., Heatherington, J. & Freeman, R. (2002a) Rapid real-time PCR for determination of penicillin susceptibility in pneumococcal meningitis, including culture-negative cases. *J Clin Microbiol*, 40, 682-684.

Kearns, A.M., Draper, B., Wipat, W., Turner, A.J., Wheeler, J., Freeman, R., Harwood, J., Gould, F.K. & Dark, J.H. (2001a) LightCycler-based quantitative PCR for detection of cytomegalovirus in blood, urine, and respiratory samples. *J Clin Microbiol*, 39, 2364-2365.

Kearns, A. M., R. Freeman, O. M. Murphy, P. R. Seiders, M. Steward, and J. Wheeler. 1999. Rapid PCR-based detection of *Streptococcus pneumoniae* DNA in cerebrospinal fluid. J. Clin. Microbiol. 37:3434.

Lareu, M.V. & Ruiz-Ponte, C. (2004) Genotyping SNPs With the LightCycler. *Methods Mol Biol*, 297, 127-140.

Lu, J.-J., C.-L. Perng, S.-Y. Lee, and C.-C. Wan. 2000. Use of PCR with universal primers and restriction endonuclease digestions for detection and identification of common bacterial pathogens in cerebrospinal fluid. J. Clin. Microbiol. 38:2076-2080.

Morrison, K. E., D. Lake, J. Crook, G. M. Carlone, E. Ades, R. Facklam, and J. S. Sampson. 2000. Confirmation of *psaA* in all 90 serotypes of *Streptococcus pneumoniae* by PCR and potential of this assay for identification and diagnosis. J. Clin. Microbiol. 38:434-437.

Olive, D. M., and P. Bean. 1999. Principles and applications of methods for DNA-based typing of microbial organisms. J. Clin. Microbiol. 37:1661-1669.

O'Neill, A. M., S. H. Gillespie, and G. C. Whiting. 1999. Detection of penicillin susceptibility in *Streptococcus pneumoniae* by *pbp2b* PCR-restriction fragment length polymorphism analysis. J. Clin. Microbiol. 37:157-160.

Perandin, F., Manca, N., Calderaro, A., Piccolo, G., Galati, L., Ricci, L., Medici, M.C. Arcangeletti, M.C., Snounou, G., Dettori, G. & Chezzi, C. (2004) Development of a real-time PCR assay for detection of *Plasmodium falciparum, Plasmodium vivax,* and *Plasmodium ovale* for routine clinical diagnosis. *J Clin MIcrobiol*, 42, 1214-1219.

Pfaffl, M.W. (2001) A new mathematical model for relative quantification in real-time RT-PCR. *Nucleic Acids Res*. 29, e45.

Pozzi, G., M. R. Oggioni, and A. Tomasz. 1989. DNA probe for identification of *Streptococcus pneumoniae*. J. Clin. Microbiol. 27:370-372.

Raja, S., El-Hefnawy, T., Kelly, L.A., Chestney, M.L., Luketich, J.D. & Godfrey, T.E. (2002) Temperature-controlled primer limit for multiplexing of rapid, quantitative reverse transcription-PCR assays: application to intraoperative cancer diagnostics. *Clin Chem*, 48, 1329-1337.

Rajeevan, M.S., Vernon, S.D. Taysavang, N. & Unger, E.R. (2001) Validation of array-based gene expression profiles by real-time (kinetic) RT-PCR. *J Mol Diagn*, 3, 26-31.

Read, S.J., Mitchell, J.L. & Fink, C.G. (2001) LightCycler multiplex PCR for the laboratory diagnosis of common viral infections of the central nervous system. *J Clin Microbiol*, 39, 3056-3059.

Rickert, A.M., Lehrach, H. & Sperling, S. (2004) Multiplexed real-time PCR using universal reporters. *Clin Chem*, 50, 1680-1683.

Rudolph, K. M., A. J. Parkinson, C. M. Black, and L. W. Mayer. 1993. Evaluation of polymerase chain reaction for diagnosis of pneumococcal pneumonia. J. Clin. Microbiol. 31:2661-2666.

Salo, P., A. Ortqvist, and M. Leinonen. 1995. Diagnosis of bacteremic pneu-mococcal pneumonia by amplification of pneumolysin gene fragment in serum. J. Infect. Dis. 171-479-482.

Sanchez, J.A., Pierce, K.E., Rice, J.E. & Wangh, L.J. (2004) Linear-after-the-exponential (LATE)-PCR: an advanced method of asymmetric PCR and its uses in quantitative real-time analysis. *Proc Natl Acad Sci U S A*, 101, 1933-1938.

Siraj, A.K., Ozbek, U., Sazawal, S., Sirma, S., Timson, G., Al-Nasser, A., Bhargava, M., El Solh, H., Bhatia, K. & Gutierrez, M.I. (2002) Preclinical validation of a monochrome real-time multiplex assay for translocations in childhood acute lymphoblastic leukemia. *Clin Cancer Res*, 8, 3832-3840.

Smith, A. M., and K. P. Klugman. 1998. Alterations in PBP 1A essential for high-level penicillin resistance in *Streptococcus pneumoniae*, Antimicrob. Agents Chemother. 42:1329-1333.

Solinas, A., Brown, L.J., McKeen, C., Mellor, J.M., Nicol, J., Thelwell, N. & Brown, T. (2001) Duplex Scorpion primers in SNP analysis and FRET applications. *Nucleic Acids Res*, 29, E96.

Song, P., Li, S., Meibohm, B., Gaber, A.O., Honaker, M.R., Kotb, M. & Yates, C.R. (2002) Detection of MDR1 single nucleotide polymorphisms C3435T and G2677T using real-time polymerase chain reaction: MDR1 single nucleotide polymorphism genotyping assay. *AAPS PharmSci*, 4, E29.

Svanvik, N., Stahlberg, A., Sehlstedt, U., Sjoback, R. & Kubista, M. (2000) Detection of PCR products in real time using light-up probes. *Anal Biochem*, 287, 179-182.

Thomassin, H., Kress, C. & Grange, T. (2004) MethylQuant: a sensitive method for quantifying methylation of specific cytosines within the genome. *Nucleic Acids Res*, 32, e168.

Toikka, P., S. Nikkari, O. Ruuskanen, M. Leinonen, and J. Mertsola. 1999. Pneumolysin PCR-based diagnosis of invasive pneumococcal infection in children. J. Clin. Microbiol. 37:633-637.

Tung, C.H., Mahmood, U., Bredow, S. & Weissleder, R. (2000) In vivo imaging of proteolytic enzyme activity using a novel molecular reporter. *Cancer Res*, 60, 4953-4958.

Ubukata, K., Y. Asahi, A. Yamane, and M. Konno. 1996. Combinational detection of autolysin and penicillin-binding protein 2B genes of *Streptococcus pneumoniae* by PCR. J. Clin. Microbiol. 34:592-596.

Uhl, J.R., Bell, C.A., Sloan, L.M., Espy, M.J., Smith, T.F., Rosenblatt, J.E. & Cockerill, F.R., 3rd (2002) Application of rapid-cycle real-time polymerase chain reaction for the detection of microbial pathogens: the Mayo-Roche Rapid Anthrax Test. *Mayo Clin Proc*, 77, 673-680.

Van Belkum, A., M. Sluijter, R. De Groot, H. Verbrugh, and P. W. M. Hermans. 1996. Novel Box repeat PCR assay for high-resolution typing of *Streptococcus pneumoniae* strains. J. Clin. Microbiol. 34:1176-1179.

van Dijk, J.P., Heuver, L.H., van der Reijden, B.A., Raymakers, R.A., de Witte, T. & Jansen, J.H. (2002) A novel, essential control for clonality analysis wtih human androgen receptor gene polymerase chain reaction. *Am J Pathol*, 161, 807-812.

Vandesompele, J., De Preter, K., Pattyn, F., Poppe, B., Van Roy, N., De Paepe, A. & Speleman, F. (2002) Accurate normalization of real-time quantitative RT-PCR data by geometric averaging of multiple internal control genes *Genome Biol*, 3, Research0034.

Vet, J.A., Majithia, A.R., Marras, S.A., Tyagi, S., Dube, S., Poiesz, B.J. & Kramer, F.R. (1999) Multiplex detection of four pathogenic retroviruses using molecular beacons. *Proc Natl Acad Sci U S A*, 96, 6394-6399.

Von Ahsen, N., Armstrong, V.W. & Oellerich, M. (2004) Rapid, Long-Range Molecular Haplotyping of Thiopurine S-methyltransferase (TPMT) *3A. *3B, and *3C. *Clin Chem*.

Vrettou, C., Traeger-Synodinos, J., Tzetis, M., Palmer, G., Sofocleous, C. & Kanavakis, E. (2004) Real-time PCR for single-cell genotyping in sickle cell and thalassemia syndromes as a rapid, accurate, reliable, and widely applicable protocol for preimplantation genetic diagnosis. *Hum Mutat*, 23, 513-521.

Wang, X. & Seed, B. (2003) A PCR primer bank for quantitative gene expression analysis. *Nucleic Acids Res*, 31, e154.

Watson, D. A., V. Kapur, D. M. Musher, J. W. Jacobson, and J. M. Musser. 1995. Identification, cloning and sequencing of DNA essential for encapsulation of *Streptococcus pneumoniae*. Curr. Microbiol. 31:251-259.

Watzinger, F., Suda, M., Preuner, S., Baumgartinger, R., Ebner, K., Baskova, L., Niesters, H.G., Lawitschka, A. & Lion, T. (2004) Real-time quantitative PCR assays for detection and monitoring of pathogenic human viruses in immunosuppressed pediatric patients. *J Clin Microbiol*, 42, 5189-5198.

Whatmore, A. M., S. J. King, N. C. Doherty, D. Sturgeon, N. Chanter, and C. G. Dowson. 1999. Molecular characterization of equine isolates of *Streptococcus pneumoniae*: natural disruption of genes encoding the virulence factors pneumolysin and autolysin. Infect. Immun. 67:2776-2782.

Whatmore, A. M., and C. G. Dowson. 1999. The autolysin-encoding gene (*lytA*) of *Streptococcus pneumoniae* displays restricted allelic variation despite localized recombination events with genes of pneumococcal bacteriophage encoding cell wall lytic enzymes. Infect. Immun. 67:4551-4556.

Whatmore, A. M., A. Efstratiou, A. P. Pickerill, K. Broughton, G. Woodard, D. Sturgeon, R. George, and C. G. Dowson. 2000. Genetic relationships between clinical isolates of *Streptococcus pneumoniae, Streptococcus oralis*, and *Streptococcus mitis*: characterization of "atypical" pneumococci and organisms allied to *S. mitis* harboring *S. pneumoniae* virulence factor-encoding genes. Infect. Immun. 68:1374-1382.

Wheeler, J., R. Freeman, M. Steward, K. Henderson, M. J. Lee, N. H. Piggott, G. J. Eltringham, and A. Galloway. 1999. Detection of pneumolysin in sputum. J. Med. Microbiol. 48:863-866.

Wittwer, C.T., Reed, G.H., Gundry, C.N., Vandersteen, J.G. & Pryor, R.J. (2003) high-resolution genotyping by amplicon melting analysis using LCGreen. *Clin Chem*, 49, 853-860.

Zhang, Y., D. J. Isaacman, R. M. Wadowsky, J. Rydquist-Whtie, J. C. Post, and G. D. Ehrlich. 1995. Detection of *Streptococcus pneumoniae* in whole blood by PCR. J. Clin. Microbiol. 33:596-601.

Zimmermann, B., Holzgreve, W., Wenzel, F. & Hahn, S. (2002) Novel real-time quantitative PCR test for trisomy 21. *Clin Chem*, 48, 362-363.

Berry et al., "Sequence Heterogeneity of PsaA, a 37-Kilodalton Putative Adhesin Essential for Virulence of *Streptococcus pneumoniae*,"*Infection and Immunity*, 64(12):5255-5262 (1996).

Greiner et al., "Quantitative Detection of *Streptococcus pneumoniae* in Nasopharyngeal Secretions by Real-Time PCR," *Journal of Clinical Microbiology*, 39(9):3129-3134 (2001).

McAvin et al., "Sensitive and Specific Method for Rapid Indentification of *Streptococcus pneumoniae* Using Real-Time Fluorescence PCR," *Journal of Clinical Microbiology*, 39(10):3446-3451 (2001).

Morrison et al., "Confirmation of psa A in All 90 Sertypes of *Strptococcus pneumoniae* by PCR and Potential of This Assay for Indentification and Diagnosis," *Journal of Clinical Microbiology*, 38(1):434-437 (2000).

Scott et al., "Diagnosis of Pneumococcal Pneumonia by *psaA* PCR Analysis of Lung Aspirates from Adult Patients in Kenya," *Journal of Clincal Microbiology*, 41(6):2554-2559 (2003).

* cited by examiner

SEQUENCE LISTING

<160> NUMBER OF SEQ ID NOS: 11

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:/note=
     synthetic construct

<400> SEQUENCE: 1
gccctaataa attggaggat ctaatga                                       27

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:/note=
     synthetic construct

<400> SEQUENCE: 2
gaccagaagt tgtatctttt tttccg                                       26

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:/note= synthetic construct

<400> SEQUENCE: 3
ctagcacatg ctacaagaat gattgcagaa agaaa                                   35

<210> SEQ ID NO 4
<211> LENGTH: 1330
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 4
tactgcttca gttttgggac tctttattgg ctatagtttt aatgttgcgg caggttctag        60
tatcgtgctt acagctgcta gtttctttct cattagcttc tttatcgctc ccaaacaacg       120
atatttgaaa ctgaaaaata aacatttgtt aaaataaggg gcaaagccct aataaattgg       180
aggatctaat gaaaaaatta ggtacattac tcgttctctt tctttctgca atcattcttg       240
tagcatgtgc tagcggaaaa aaagatacaa cttctggtca aaaactaaaa gttgttgcta       300
caaactcaat catcgctgat attactaaaa atattgctgg tgacaaaatt gaccttcata       360
gtatcgttcc gattgggcaa gacccacacg aatacgaacc acttcctgaa gacgttaaga       420
aaacttctga ggctgatttg attttctata acggtatcaa ccttgaaaca ggtggcaatg       480
cttggtttac aaaattggta gaaaatgcca agaaaactga aaacaaagac tacttcgcag       540
tcagcgacgg cgttgatgtt atctaccttg aaggtcaaaa tgaaaaagga aaagaagacc       600
cacacgcttg gcttaacctt gaaaacggta ttatttttgc taaaaatatc gccaaacaat       660
tgagcgccaa agaccctaac aataaagaat tctatgaaaa aaatctcaaa gaatatactg       720
ataagttaga caaacttgat aaagaaagta aggataaatt taataagatc cctgctgaaa       780 agaaaactcat tgtaaccagc gaaggagcat tcaaatactc tctaaagcc tatggtgtcc        840 caagtgccta catctgggaa atcaatactg aagaagaagg aactcctgaa caaatcaaga       900
ccttggttga aaaacttcgc caaacaaaag ttccatcact cttttgtagaa tcaagtgtgg      960 atgaccgtcc aatgaaaact gtttctcaag acacaaacat cccaatctac gcacaaatct      1020
ttactgactc tatcgcagaa caaggtaaag aaggcgacag ctactacagc atgatgaaat      1080
acaaccttga caagattgct gaaggattgg caaaataagc ctctgaaaaa cgtcattctc      1140
atgtgagctg gcgttttttc tatgcccaca tttccggtca aatcattgga aaattctgac      1200
tgtttcagat acaatggaag aaaaaagatt ggagtatcct atggtaactt ttctcggaaa      1260
tcctgtgagc tttacaggta aacaactaca agtcggcgac aaggcgcttg attttttctct      1320 tactacaaca                                                             1330

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 5
tcattagatc ctccaatttta ttagggc                                          27

<210> SEQ ID NO 6
<211> LENGTH: 26

```
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 6
cggaaaaaaa gatacaactt ctggtc                                        26

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 7
tttctttctg caatcattct tgtagcatgt gctag                              35

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 8
gccctaataa attggaggat ctaatga                                       27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 9
ttgaccagaa gttgtatctt ttttcc                                        27

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 10
ccctaataaa ttggaggatc taatgaaa                                      28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 11
caacttttag ttttgaccag aagttgta                                      28
```

DEVELOPMENT OF A REAL-TIME PCR ASSAY FOR DETECTION OF PNEUMOCOCCAL DNA AND DIAGNOSIS OF PNEUMOCOCCCAL DISEASE

I. BACKGROUND

*Streptococcus pneumoniae* is the leading cause of community-acquired pneumonia, meningitis, and otitis media in the United States (Brown et al., 1998). While traditional antimicrobial therapy has proven an effective treatment in the past, the emergence of penicillin- and multidrug-resistant strains has resulted in an increasing number of cases of illnesses and fatalities (Doern et al., 1999; Jacoby, 1996). Pneumococcal isolation and identification are complicated by antimicrobial suppression of growth in culture and contamination by normal flora alpha-streptococci. Detection by classical techniques, culture, and serological methods can be time-consuming and indeterminate. Sensitive and specific assays that can be completed quickly in the clinical laboratory are essential for early diagnosis and effective therapy. Molecular assays are inherently valuable because detection can be achieved with enhanced sensitivity and specificity, and detection is not diminished with nonviable organisms. Various molecular methods have been employed to assist investigations (Gillespie, 1999; Hall, 1998; Olive and Bean, 1999).

Accurate pneumococcal disease diagnosis has been frequently hampered not only by the difficulties in obtaining isolates of the organism from patient specimens, but also by the misidentification of *Pneumococcus*-like viridans streptococci species (P-LVS) as *Streptococcus pneumoniae* (Spn). This is especially critical when the considered specimen comes from respiratory site.

A major area of focus in pneumococcal disease research has been in vaccine development. The failure of the licensed 23-valent polysaccharide vaccine to provide protection in young children (<2 years of age), the elderly, or the immunocompromised (Forrester et al., 1987) led to development of a second-generation protein-conjugate vaccine, soon to be licensed. This vaccine, composed of the seven most frequent invasive disease-causing capsular serotypes, may overcome the problems of poor immunogenicity associated with the 23-valent vaccine. However, there are indications that this protein-conjugate vaccine may not prevent replacement carriage of serotypes not contained in the vaccine (Obaro et al., 1996). These concerns, along with reports of an increase in antibiotic-resistant pneumococci (Centers for Disease Control and Prevention, 1997), have shifted interest towards the development of a vaccine based on immunogenic pneumococcal species-common proteins of *S. pneumoniae* (Hammerschmidt et al., 1997). The most promising of these proteins include pneumolysin (Paton, 1996), pneumococcal surface protein (PspA) (Briles et al., 1988), and of particular focus in this study, pneumococcal surface adhesin A (PsaA) (Sampson et al., 1994).

PsaA, encoded by the psaA gene, is a 37-kDa surface protein first identified by Russell et al. (Russell et al., 1990). Monoclonal antibody studies suggest that PsaA is expressed in all 90 serotypes of *S. pneumoniae* (Crook et al., 1998), and PCR-restriction fragment length polymorphism analysis of the 23 vaccine serotypes demonstrated the conservation of the psaA gene (Sampson et al., 1997).

II. SUMMARY

Disclosed are methods and compositions related to the detection of pneumococcal DNA and the diagnosis of pneumococcal disease. More specifically, disclosed is a real-time PCR method for detection of the pneumococcal surface adhesion protein (psaA) gene.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 2:
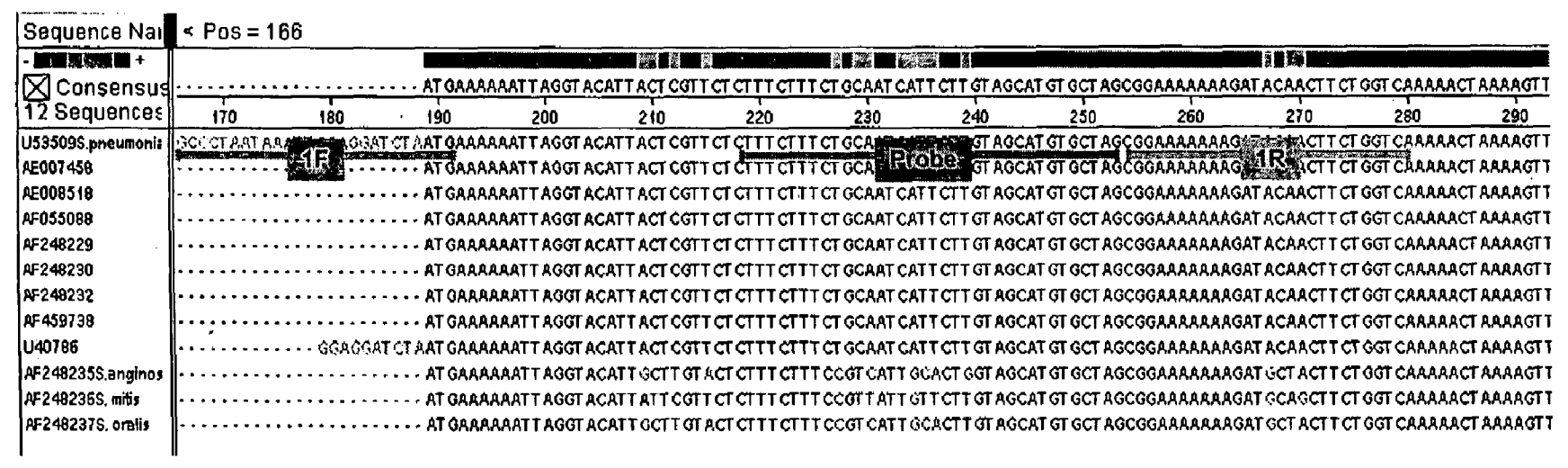

FIG. 2 shows the location of the forward and reverse primers and probe used to detect the psaA gene of *Streptococcus pneumoniae*

IV. DETAILED DESCRIPTION

Figure 1:
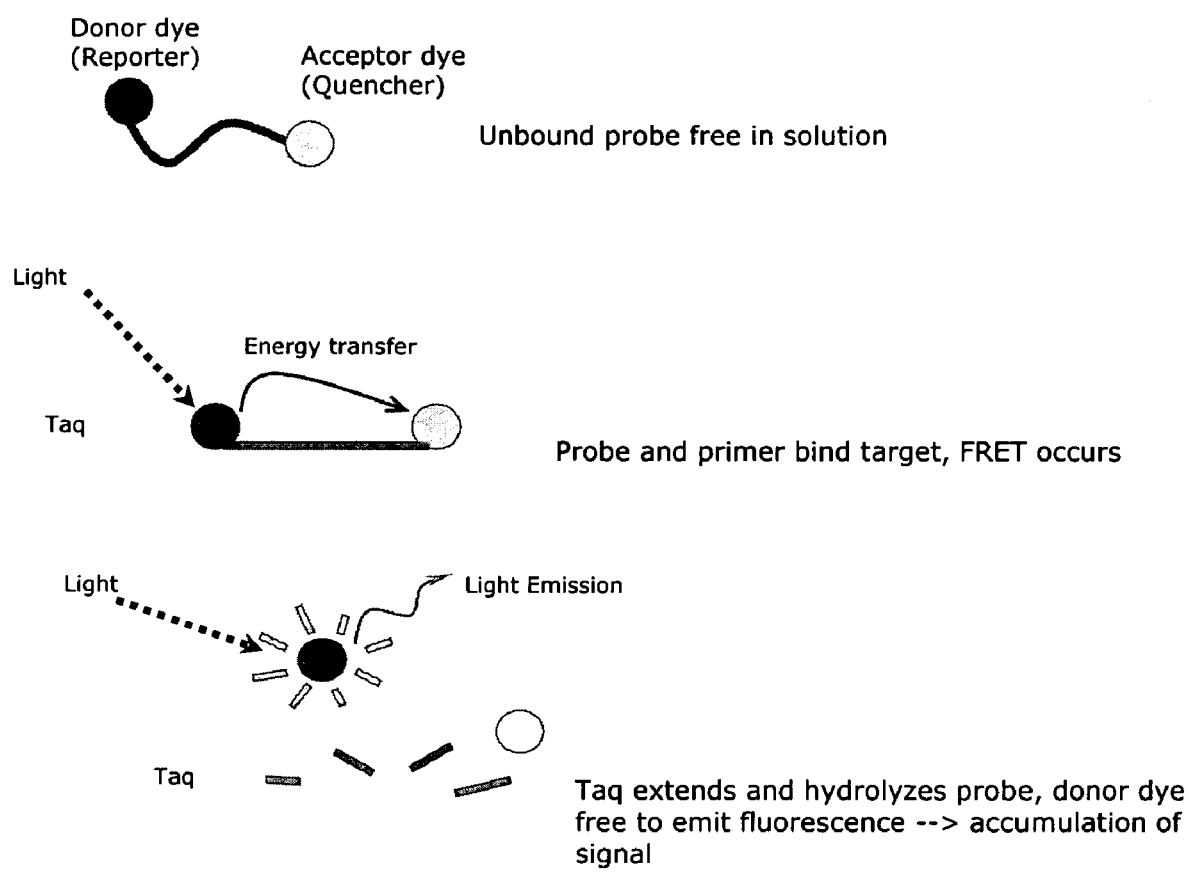
FIG. 1 shows the general method of using TaqMan™ probes in a real-time PCR reaction to detect a sequence of interest.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10"as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Polymerase Chain Reaction is abbreviated as "PCR". The term "real-time PCR" is intended to mean any amplification technique which makes it possible to monitor the evolution of an ongoing amplification reaction.

A "subject" is an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and more preferably, a human.

As used herein, "stringent conditions" refers to the washing conditions used in a hybridization protocol. In general, the washing conditions should be a combination of temperature and salt concentration chosen so that the denaturation temperature is approximately 5-20° C. below the calculated Tm (the melting temperature at which half of the molecules dissociate from their hybridization partners) of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The Tm of such an oligonucleotide can be estimated by allowing 2° C. for each A or T nucleotide, and 4° C. for each G or C. For example, an 18 nucleotide probe of 50% G+C would, therefore, have an approximate Tm of 54° C. Stringent conditions are known to one of skill in the art. See, for example, Sambrook et al. (2001). An example of stringent wash conditions is 4×SSC at 65° C. Highly stringent wash conditions include, for example, 0.2×SSC at 65° C.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a particular probe is disclosed and discussed and a number of modifications that can be made to a number of molecules including the probe are discussed, specifically contemplated is each and every combination and permutation of probes and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. For example GCCCTAATAAATTGGAGGATCTAATGA (SEQ ID NO: 1), GACCAGAAGTTGTATCTTTTTTTCCG (SEQ ID NO: 2) and CTAGCACATGCTACAAGAATGATTGCA-GAAAGAAA (SEQ ID NO: 3) set forth particular sequences of a primer set and a probe, respectively, for specific and sensitive amplification and detection of psaA. Specifically disclosed are variants of these and other genes and proteins herein disclosed which have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Hybridization/Selective Hybridization

The term hybridization typically means a sequence driven interaction between at least two nucleic acid molecules, such as a primer or a probe and a gene or a portion of a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically-manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein. Examples of specific hybridization conditions are provided herein. For the reasons stated above, these conditions are exemplary only and do not limit the real-time PCR method described.

3. Nucleic Acids

There are a variety of molecules disclosed herein that are nucleic acid based, including for example the primers and probe that hybridize specifically to the psaA gene of *Streptococcus pneumoniae*. The disclosed nucleic acids are made up of for example, nucleotides, nucleotide analogs, or nucleotide substitutes. Non-limiting examples of these and other molecules are discussed herein. It is understood that for example, when a vector is expressed in a cell that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1, 2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525, 465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

One particular sequence set forth in SEQ.ID. NO. 1 is used herein, as an example of a disclosed primer. One particular sequence set forth in SEQ ID NO: 2 is an example of an additional disclosed primer. One particular sequence set forth in SEQ ID NO: 3 is an example of a disclosed probe. Primers and/or probes can be designed to be specific for psaA sequences given the information disclosed herein. There are a variety of sequences related to, for example, psaA as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the psaA gene disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the psaA gene or region of the psaA gene or they hybridize with the complement of the psaA gene or complement of a region of the psaA gene.

The size of the primers or probes for interaction with the psaA gene in certain embodiments can be any size that supports the desired enzymatic manipulation of the primer, such as DNA amplification or the simple hybridization of the probe or primer. A typical psaA primer or probe would be at least 15, 16, 17, 18, 19, 20, 21, 22, 23, 24, 25, 26, 27, 28, 29, or 30 nucleotides long.

In other embodiments a psaA primer or probe can be less than or equal to 15, 16, 17, 18, 19, 20, 21, 22, 23, 24, 25, 26, 27, 28, 29, or 30 nucleotides long.

In certain embodiments the primers and probes are designed such that they are outside primers whose nearest point of interaction with the psaA gene is within 0, 1, 2, 3, 4, 5, 6, 7, 8, 9, 10, 11, 12, 13, 14, 15, 16, 17, 18, 19, 20, 21, 22, 23, 24, 25, 26, or 27 nucleotides of the outermost defining nucleotides of the SEQ ID NO: 3.

For example, with respect to the psaA gene set forth in SEQ ID NO: 4 (GenBank Accession Number U53509), certain embodiments of the primers or probes would be designed such that they are outside primers whose nearest point of interaction with the psaA gene occurs at position 217 and 254, respectively, of SEQ ID NO: 4.

The primers for the psaA gene typically will be used to produce an amplified DNA product that contains a region of the psaA gene between position 166 and 280 of SEQ ID NO: 4. In general, typically the size of the product will be such that the size can be accurately determined to within 3, or 2 or 1 nucleotides.

In certain embodiments this product is at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or 114 nucleotides long.

In other embodiments the product is less than or equal to 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or 114 nucleotides long.

Also disclosed is a sense primer that is an oligonucleotide comprising SEQ ID NO: 1 or a sequence that hybridizes, under conditions suitable for a polymerase chain reaction, with: 5'-TCATTAGATCCTCCAATTTATTAGGGC-3' (SEQ ID NO: 5); or a sequence complementary thereto, wherein the oligonucleotide is from 15-30 consecutive nucleotides.

Also disclosed is an antisense primer that is an oligonucleotide, comprising at least 15 consecutive nucleotides of SEQ ID NO: 2 or a sequence that hybridizes, under conditions suitable for a polymerase chain reaction, with: 5'-CGGAAAAAAAGATACAACTTCTGGTC-3' (SEQ ID NO: 6); or a sequence complementary thereto, wherein the oligonucleotide is from 15-30 consecutive nucleotides.

Also disclosed is a nondegenerate probe that is an oligonucleotide, comprising at least 20 consecutive nucleotides of SEQ ID NO: 3 or a sequence that hybridizes, under conditions suitable for a polymerase chain reaction, with: 5'-TTTCTTTCTGCAATCATTCTTGTAGCATGTGCTAG-3' (SEQ ID NO: 7); or a sequence complementary thereto. Also disclosed is a nondegenerate probe that is an oligonucleotide, comprising: 5'-X-CTAGCACATGC"T"ACAAGAATGATTGCAGAAAGAAA-Y-3', wherein X is a fluorophore, wherein Y is a phosphate group or phosphate groups, wherein "T" is a thymine with a dark quencher or acceptor dye linked to it.

In some embodiments, the fluorophore can be carboxyfluorescein (HEX), Fam, Joe, 6-carboxy-X-rhodamine (Rox), Texas Red, or Cy 5.

Also, in some embodiments, 1, 2, 3, 4, 5, 6, or 7 phosphate groups can be attached to the 3' end of the probe.

In some embodiments, the dark quencher is attached to the "T" residue of the probe can be a Black hole quencher (BHQ1-dT), Dabcyl-dT (Glen Research) or QSY7 (Molecular probes) via an aminolink modified-dT.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of psaA (e.g., mRNA encoded by SEQ ID NO: 4) or the genomic DNA of psaA (e.g., SEQ ID NO: 4) or they can interact with the polypeptide PsaA encoded by SEQ ID NO: 4. Often, functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Patents: U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. For example, when determining the specificity of psaA aptamers, the background protein could be GADPH. Representative examples of how to make and use aptamers to bind a variety of different target molecules can be found in the following non-limiting list of U.S. Patents: U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Patents: U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Patents: U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Patents: U.S. Pat. Nos. 5,595,873 and 5,652,107). There are also a number of ribozymes that are not found in natural systems, but which have been engineered to catalyze specific reactions de novo (for example, but not limited to the following U.S. Patents: U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Patents: U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. patents: U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukaryotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in the following non-limiting list of U.S. Patents: U.S. Pat. Nos. 5,168,053, 5,624,824, 5,683,873, 5,728,521, 5,869,248, and 5,877,162.

4. Peptides a) Protein Variants

As discussed herein there are different *Streptococcus pneumonia* serotypes that contain variants of the PsaA protein that are known and herein contemplated. The methods disclosed herein have the advantage of detecting all *Streptococcus pneumonia* serotypes.

5. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

6. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums, comprising the sequences and information regarding the sequences set forth herein. Also disclosed are computer readable mediums, comprising the sequences and information regarding the sequences set forth herein.

7. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit comprising reagents for real-time PCR-type amplification reaction for detecting *Streptococcus pneumoniae*, comprising sense primers, antisense primers and a nondegenerate probe. For example the kit can detect the psaA gene of *Streptococcus pneumoniae*.

Also disclosed is a kit comprising reagents for real-time PCR-type amplification reaction for detecting *Streptococcus pneumoniae*, comprising sense primers, antisense primers and a nondegenerate probe wherein the sense primer is an oligonucleotide comprising SEQ ID NO: 1 or a sequence that hybridizes, under conditions suitable for a polymerase chain reaction, with: SEQ ID NO: 5; or a sequence complementary thereto, wherein the oligonucleotide is from 15-30 consecutive nucleotides and, wherein the antisense primer is an oligonucleotide, comprising at least 15 consecutive nucleotides of SEQ ID NO: 2 or a sequence that hybridizes, under conditions suitable for a polymerase chain reaction, with: SEQ ID NO: 6; or a sequence complementary thereto, wherein the oligonucleotide is from 15-30 consecutive nucleotides and, wherein the nondegenerate probe is an oligonucleotide, comprising at least 20 consecutive nucleotides of SEQ ID NO: 3 or a sequence that hybridizes, under conditions suitable for a polymerase chain reaction, with: SEQ ID NO: 7; or a sequence complementary thereto. The disclosed kits can include any of the probes as defined herein, for example a probe having a fluorophore attached to the 5' end of the probe, wherein at least one phosphate group is attached to the 3' end of the probe, and wherein a dark quencher is attached to the "T" residue of the probe.

Also disclosed is a kit comprising reagents for real-time PCR-type amplification reaction for detecting *Streptococcus pneumoniae*, comprising sense primers, antisense primers and a nondegenerate probe wherein the sense primer is an oligonucleotide comprising SEQ ID NO: 1 or a sequence that hybridizes, under conditions suitable for a polymerase chain reaction, with: SEQ ID NO: 5; or a sequence complementary thereto, wherein the oligonucleotide is from 15-30 consecutive nucleotides.

Also disclosed is a kit comprising reagents for real-time PCR-type amplification reaction for detecting *Streptococcus pneumoniae*, comprising sense primers, antisense primers and a nondegenerate probe wherein the antisense primer is an oligonucleotide, comprising at least 15 consecutive nucleotides of SEQ ID NO: 2 or a sequence that hybridizes, under conditions suitable for a polymerase chain reaction, with: SEQ ID NO: 6; or a sequence complementary thereto.

Also disclosed is a kit comprising reagents for real-time PCR-type amplification reaction for detecting *Streptococcus pneumoniae*, comprising sense primers, antisense primers and a nondegenerate probe wherein the nondegenerate probe is an oligonucleotide, comprising at least 20 consecutive nucleotides of SEQ ID NO: 3 or a sequence that hybridizes, under conditions suitable for a polymerase chain reaction, with: SEQ ID NO: 7; or a sequence complementary thereto. The disclosed kits can include any of the probes as defined herein, for example a probe having a fluorophore attached to the 5' end of the probe, wherein at least one phosphate group is attached to the 3' end of the probe, and wherein a dark quencher is attached to the "T" residue of the probe.

8. Compositions with Similar Functions

It is understood that the compositions disclosed herein have certain functions, such as priming DNA synthesis or binding psaA. Disclosed herein are certain structural requirements for performing the disclosed functions, and it is understood that there are a variety of structures which can perform the same function which are related to the disclosed structures, and that these structures will ultimately achieve the same result, for example priming DNA synthesis or binding psaA.

C. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Process for Making the Compositions

Disclosed are processes for making the compositions as well as making the intermediates leading to the compositions. For example, disclosed are nucleic acids in SEQ ID NOS: 1, 2, and 3.

There are a variety of methods that can be used for making these compositions, such as synthetic chemical methods and standard molecular biology methods. It is understood that the methods of making these and the other disclosed compositions are specifically disclosed.

Also disclosed are nucleic acid molecules produced by the process comprising linking in an operative way a nucleic acid molecule comprising a sequence having at least 80% identity to a sequence set forth in SEQ ID NOS: 1, 2, and 3, and a sequence controlling the expression of the nucleic acid.

Also disclosed are nucleic acid molecules produced by the process comprising linking in an operative way a nucleic acid molecule comprising SEQ ID NO: 3 to a fluorophore on the 5' end.

Also disclosed are nucleic acid molecules produced by the process comprising linking in an operative way a nucleic acid molecule comprising SEQ ID NO: 3 to phosphate moitieties on the 3' end.

Also disclosed are nucleic acid molecules produced by the process comprising linking in an operative way a nucleic acid molecule comprising SEQ ID NO: 3 (CTAGCACATGC-"T"ACAAGAATGATTGCAGAAAGAAA) to a dark quencher on the internal "T" residue of SEQ ID NO: 3. The dark quencher molecule can be linked to the probe by an amino linkage, however any standard method of attaching a dark quencher to an internal "T" residue can be used in this method.

D. Methods of Using the Compositions

1. Methods of Using the Compositions as Research Tools

The disclosed compositions, either alone or in combination, can be used in a variety of ways. For example, the disclosed compositions, such as SEQ ID NOS: 1, 2, and 3 either alone or in combination can be used to detect the presence of the psaA gene.

The compositions, either alone or in combination, can also be used to detect *Streptococcus pneumoniae* serotypes, for example, *Streptococcus pneumoniae* infections.

The disclosed compositions, either alone or in combination, can also be used to differentiate between true *Streptococcus pneumoniae* species and Pneumococcus-like viridian streptococci species.

Pneumococcus-like viridian streptococci species include: *S. pseudopneumoniae, S. mitis, S. oralis, S. sanguinis, S. parasanguinis, S. peroris, S. infantis, S. gordonii, S. cristatus, S. salivarius, S. vestibularis, S. australis, S. sinensis, S. oligofermentans, S. intestinalis*); and other upper respiratory organisms such as *S. pyogenes, S. agalactiae, Staphylococcus aureus, Dolosigranulum pigrum, Enterococcus faecalis*, and *Escherichia coli*.

The disclosed compositions, either alone or in combination, can also be used in any known method for isolating or identifying single nucleotide polymorphisms. The compositions can also be used in any known way of using the computer readable embodiments of the disclosed compositions, for example, to study relatedness or to perform molecular modeling analysis related to the disclosed compositions.

The disclosed compositions, either alone or in combination, can also be used as compositions for carrying out a polymerase chain reaction (PCR).

The disclosed compositions, either alone or in combination, can also be used as compositions for carrying out a real-time PCR reaction.

The disclosed compositions, either alone or in combination, can also be used to differentially detect the presence true *Streptococcus pneumoniae* from Pneumococcus-like viridian streptococci species.

a) Polymerase Chain Reaction (PCR)

The technology of PCR permits amplification and subsequent detection of minute quantities of a target nucleic acid. Details of PCR are well described in the art, including, for example, U.S. Pat. Nos. 4,683,195 to Mullis et al., U.S. Pat. No. 4,683,202 to Mullis and U.S. Pat. No. 4,965,188 to Mullis et al. Generally, oligonucleotide primers are annealed to the denatured strands of a target nucleic acid, and primer extension products are formed by the polymerization of deoxynucleoside triphosphates by a polymerase. A typical PCR method involves repetitive cycles of template nucleic acid denaturation, primer annealing and extension of the annealed primers by the action of a thermostable polymerase. The process results in exponential amplification of the target nucleic acid, and thus allows the detection of targets existing in very low concentrations in a sample. PCR is widely used in a variety of applications, including biotechnological research, clinical diagnostics and forensics.

b) Real-Time PCR

In implementing the present invention, reference may optionally be made to a general review of PCR techniques and to the explanatory note entitled "Quantitation of DNA/RNA Using Real-Time PCR Detection" published by Perkin Elmer Applied Biosystems (1999) and to PCR Protocols (Academic Press New York, 1989).

Real-time PCR monitors the fluorescence emitted during the reaction as an indicator of amplicon production during each PCR cycle (ie, in real time) as opposed to the endpoint detection (For example see FIG. 1; Higuchi, 1992; Higuchi, 1993). The real-time progress of the reaction can be viewed in some systems.

The real-time PCR system is based on the detection of a fluorescent reporter (Lee, 1993; Livak, 1995). This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

A fixed fluorescence threshold is set significantly above the baseline that can be altered by the operator. The parameter $C_T$ (threshold cycle) is defined as the cycle number at which the fluorescence emission exceeds the fixed threshold.

There are three main fluorescence-monitoring systems for DNA amplification (Wittwer, 1997(a)): (1) hydrolysis probes; (2) hybridising probes (see *Hybridisation Probe Chemistry*, incorporated herein by reference for its teaching of fluorescence monitoring systems); and (3) DNA-binding agents (Wittwer, 1997; van der Velden, 2003, incorporated herein for their teaching of DNA-binding agents). Hydrolysis probes include TaqMan™ probes (Heid et al, 1996, incorporated herein by reference for its teaching of hydrolysis probes), molecular beacons (Mhlanga, 2001; Vet, 2002; Abravaya, 2003; Tan, 2004; Vet & Marras, 2005, incorporated herein by reference for their teaching of molecular beacons) and scorpions (Saha, 2001; Solinas, 2001; Terry, 2002, incorporated herein by reference for their teaching of scorpions). They use the fluorogenic 5' exonuclease activity of Taq polymerase to measure the amount of target sequences in cDNA samples (see also Svanvik, 2000, incorporated herein by reference for its teaching of light-up probes).

TaqMan™ probes are oligonucleotides longer than the primers (20-30 bases long with a Tm value of 10° C. higher) that contain a fluorescent dye usually on the 5' base, and a quenching dye typically on the 3' base. When irradiated, the excited fluorescent dye transfers energy to the nearby quenching dye molecule (this is called FRET=Förster or fluorescence resonance energy transfer) (Hiyoshi, 1994; Chen, 1997). Thus, the close proximity of the reporter and quencher prevents detection of any fluorescence while the probe is intact. TaqMan™ probes are designed to anneal to an internal region of a PCR product. When the polymerase replicates a template on which a TaqMan™ probe is bound, its 5' exonuclease activity cleaves the probe (Holland, 1991). This ends the activity of quencher (no FRET) and the reporter dye starts to emit fluorescence which increases in each cycle proportional to the rate of probe cleavage. Accumulation of PCR products is detected by monitoring the increase in fluorescence of the reporter dye (note that primers are not labelled). TaqMan™ assay uses universal thermal cycling parameters and PCR reaction conditions. Because the cleavage occurs only if the probe hybridises to the target, the origin of the detected fluorescence is specific amplification. The process of hybridisation and cleavage does not interfere with the exponential accumulation of the product. One specific requirement for fluorogenic probes is that there be no G at the 5' end. A 'G' adjacent to the reporter dye can quench reporter fluorescence even after cleavage.

Molecular beacons also contain fluorescent (FAM, TAMRA, TET, ROX) and quenching dyes (typically DABCYL) at either end but they are designed to adopt a hairpin structure while free in solution to bring the fluorescent dye and the quencher in close proximity for FRET to occur. They have two arms with complementary sequences that form a very stable hybrid or stem. The close proximity of the reporter and the quencher in this hairpin configuration suppresses reporter fluorescence. When the beacon hybridises to the target during the annealing step, the reporter dye is separated from the quencher and the reporter fluoresces (FRET does not occur). Molecular beacons remain intact during PCR and must rebind to target every cycle for fluorescence emission. This will correlate to the amount of PCR product available. All real-time PCR chemistries allow detection of multiple DNA species (multiplexing) by designing each probe/beacon with a spectrally unique fluor/quench pair as long as the platform is suitable for melting curve analysis. By multiplexing, the target(s) and endogenous control can be amplified in single tube. For examples, see Bernard, 1998; Vet, 1999; Lee, 1999; Donohoe, 2000; Read, 2001; Grace, 2003; Vrettou, 2004; Rickert, 2004.

With Scorpion probes, sequence-specific priming and PCR product detection is achieved using a single oligonucleotide. The Scorpion probe maintains a stem-loop configuration in the unhybridised state. The fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed.

Another alternative is the double-stranded DNA binding dye chemistry, which quantitates the amplicon production (including non-specific amplification and primer-dimer complex) by the use of a non-sequence specific fluorescent intercalating agent (SYBR-green I or ethidium bromide). It does not bind to ssDNA. SYBR green is a fluorogenic minor groove binding dye that exhibits little fluorescence when in solution but emits a strong fluorescent signal upon binding to double-stranded DNA (Morrison, 1998). Disadvantages of SYBR green-based real-time PCR include the requirement for extensive optimisation. Furthermore, non-specific amplifications require follow-up assays (melting point curve or dissociation analysis) for amplicon identification (Ririe, 1997). The method has been used in HFE-C282Y genotyping (Donohoe, 2000). Another controllable problem is that longer amplicons create a stronger signal (if combined with other factors, this may cause CCD camera saturation, see below). Normally SYBR green is used in singleplex reactions, however when coupled with melting point analysis, it can be used for multiplex reactions (Siraj, 2002).

The threshold cycle or the $C_T$ value is the cycle at which a significant increase in ΔRn is first detected (for definition of ΔRn, see below). The threshold cycle is when the system begins to detect the increase in the signal associated with an exponential growth of PCR product during the log-linear phase. This phase provides the most useful information about the reaction (certainly more important than the end-point). The slope of the log-linear phase is a reflection of the amplification efficiency. The efficiency (Eff) of the reaction can be calculated by the formula: Eff=$10^{(-1/slope)}-1$. The efficiency of the PCR should be 90-110% (−3.6>slope>−3.1). A number of variables can affect the efficiency of the PCR. These factors include length of the amplicon, secondary structure and primer quality. Although valid data can be obtained that fall outside of the efficiency range, the real time PCR should be further optimised or alternative amplicons designed. For the slope to be an indicator of real amplification (rather than signal drift), there has to be an inflection point. This is the point on the growth curve when the log-linear phase begins. It also represents the greatest rate of change along the growth curve. (Signal drift is characterised by gradual increase or decrease in fluorescence without amplification of the product.) The important parameter for quantitation is the $C_T$. The higher the initial amount of genomic DNA, the sooner accumulated product is detected in the PCR process, and the lower the $C_T$ value. The threshold should be placed above any baseline activity and within the exponential increase phase (which looks linear in the log transformation). Some software allows determination of the cycle threshold ($C_T$) by a mathematical analysis of the growth curve. This provides better run-to-run reproducibility. Besides being used for quantitation, the $C_T$ value can be used for qualitative analysis as a pass/fail measure.

In some aspects of the real time PCR method disclosed, multiplex TaqMan™ assays can be performed with ABI instruments using multiple dyes with distinct emission wavelengths. Available dyes for this purpose are FAM, TET, VIC and JOE (the most expensive). TAMRA is reserved as the quencher on the probe and ROX as the passive reference. For best results, the combination of FAM (target) and VIC (endogenous control) is recommended (they have the largest difference in emission maximum) whereas JOE and VIC should not be combined. It is important that if the dye layer has not been chosen correctly, the machine will still read the other dye's spectrum. For example, both VIC and FAM emit fluorescence in a similar range to each other and when doing a single dye, the wells should be labelled correctly. In the case of multiplexing, the spectral compensation for the post run analysis should be turned on (on ABI 7700: Instrument/Diagnostics/Advanced Options/Miscellaneous). Activating spectral compensation improves dye spectral resolution.

In addition, the real-time PCR reaction can be carried out in a wide variety of platforms including, but not limited to ABI 7700 (ABI), the LightCycler (Roche Diagnostics), iCycler (RioRad), DNA Engine Opticon ContinuousFluorescence Detection System (MJ Research), Mx400 (Stratagene), Chimaera Quantitative Detection System (Thermo Hybaid), Rotor-Gene 3000 (Corbett Research), Smartcycler (Cepheid), or the MX3000P format (Stratagene).

Disclosed is a method for detecting *Streptococcus pneumoniae* nucleic acid in a biological sample, comprising: producing an amplification product by amplifying an *Streptococcus pneumoniae* nucleotide sequence using sense primers and antisense primers, wherein said primers are chosen from oligonucleotides that hybridize, under conditions suitable for a polymerase chain reaction, with a sequence of the psaA gene of *Streptococcus pneumoniae*; and detecting said amplification product, whereby the presence of *Streptococcus pneumoniae* nucleic acid is detected.

Also disclosed is a method for detecting *Streptococcus pneumoniae* nucleic acid in a biological sample, comprising: producing an amplification product by amplifying an *Streptococcus pneumoniae* nucleotide sequence by real-time PCR using: a primer consisting of SEQ ID NO: 1 or a sequence that hybridizes, under conditions suitable for a polymerase chain reaction, with: SEQ ID NO: 5; or a sequence complementary thereto, and a primer consisting of SEQ ID NO: 2 or a sequence that hybridizes, under conditions suitable for a polymerase chain reaction, with: SEQ ID NO: 6; or a sequence complementary thereto, under conditions suitable for a polymnerase chain reaction; and detecting said amplification product by using: a probe consisting of SEQ ID NO: 3 or a sequence that hybridizes, under conditions suitable for a polymerase chain reaction, with: SEQ ID NO: 7; or a sequence complementary thereto, that hybridizes, under conditions suitable for a polymerase chain reaction, whereby the presence of *Streptococcus pneumoniae* nucleic acid is detected.

Also disclosed is a method for detecting *Streptococcus pneumoniae* nucleic acid in a biological sample, comprising: producing an amplification product by amplifying an *Streptococcus pneumoniae* nucleotide sequence by real-time PCR using: a primer consisting of SEQ ID NO: 1 or a sequence that hybridizes, under conditions suitable for a polymerase chain reaction, with: SEQ ID NO: 5; or a sequence complementary thereto, and a primer consisting of SEQ ID NO: 2 or a sequence that hybridizes, under conditions suitable for a polymerase chain reaction, with: SEQ ID NO: 6; or a sequence complementary thereto, under conditions suitable for a polymerase chain reaction; and detecting said amplification product by using: a probe consisting of SEQ ID NO: 3 or a sequence that hybridizes, under conditions suitable for a polymerase chain reaction, with: SEQ ID NO: 7; or a sequence complementary thereto, wherein a fluorophore is attached to the 5' end of the probe, wherein at least one phosphate group is attached to the 3' end of the probe, and wherein a dark quencher is attached to the "T" residue of the probe, under conditions suitable for a polymerase chain reaction, that hybridizes, under conditions suitable for a polymerase chain reaction, whereby the presence of *Streptococcus pneumoniae* nucleic acid is detected.

c) Quantifying *Streptococcus pneumoniae* Nucleic Acid in a Biological Sample

The disclosed compositions, either alone or in combination, can also be used a method for quantifying *Streptococcus pneumoniae* nucleic acid in a biological sample, comprising: producing an amplification product by amplifying an *Streptococcus pneumoniae* nucleotide sequence by real-time PCR using sense primers and antisense primers, wherein said primers are chosen from oligonucleotides that hybridize, under conditions suitable for a polymerase chain reaction, with a sequence of the psaA gene of *Streptococcus pneumoniae*; and detecting said amplification product by using a nondegenerate probe comprising an oligonucleotide that hybridizes, under conditions suitable for a polymerase chain reaction, with a sequence of the psaA gene of *Streptococcus pneumoniae*; and quantifying said amplification product in said biological sample by measuring a detection signal from said probe and comparing said detection signal to a second probe detection signal from a quantification standard, wherein said quantification standard comprises a sense probe and a nucleic acid standard.

For all of the methods described herein, a biological sample can be from any organism and can be, but is not limited to serum, peripheral blood, bone marrow specimens, embedded tissue sections, frozen tissue sections, cell preparations, cytological preparations, exfoliate samples (e.g., sputum), fine needle aspirations, amnion cells, fresh tissue, dry tissue, and cultured cells or tissue. Such samples can be obtained directly from a subject, commercially obtained or obtained via other means. Thus, the invention described herein can be utilized to analyze a nucleic acid sample that comprises genomic DNA, amplified DNA (such as a PCR product) cDNA, cRNA, a restriction fragment or any other desired nucleic acid sample. When one performs one of the herein described methods on genomic DNA, typically the genomic DNA will be treated in a manner to reduce viscosity of the DNA and allow better contact of a primer or probe with the target region of the genomic DNA. Such reduction in viscosity can be achieved by any desired methods, which are known to the skilled artisan, such as DNase treatment or shearing of the genomic DNA, preferably lightly.

2. Methods of Using the Compositions as Diagnostic Tools

The disclosed compositions, either alone or in combination, can also be used diagnostic tools related to diseases, such as pneumococcal disease. For example, the disclosed compositions, such as SEQ ID NOS: 1, 2, and 3 can be used to diagnose pneumococcal pneumoniae, by detecting the presence of the psaA gene.

The disclosed compositions, either alone or in combination, can also be used in a method for detecting *Streptococcus pneumoniae* nucleic acid in a biological sample, comprising: producing an amplification product by amplifying an *Streptococcus pneumoniae* nucleotide sequence using sense primers and antisense primers, wherein said primers are chosen from oligonucleotides that hybridize, under conditions suitable for a polymerase chain reaction, with a sequence of the psaA gene of *Streptococcus pneumoniae*; and detecting said amplification product, whereby the presence of *Streptococcus pneumoniae* nucleic acid is detected, wherein the detection of *Streptococcus pneumoniae* nucleic acid diagnoses *Streptococcus pneumoniae* infection.

The disclosed compositions, either alone or in combination, can also be used in a method for detecting *Streptococcus pneumoniae* nucleic acid in a biological sample, comprising: producing an amplification product by amplifying an *Streptococcus pneumoniae* nucleotide sequence by real-time PCR using: a primer consisting of SEQ ID NO: 1 or a sequence that hybridizes, under conditions suitable for a polymerase chain reaction, with: SEQ ID NO: 5; or a sequence complementary thereto, and a primer consisting of SEQ ID NO: 2 or a sequence that hybridizes, under conditions suitable for a polymnerase chain reaction, with: SEQ ID NO: 6; or a sequence complementary thereto, under conditions suitable for a polymerase chain reaction; and detecting said amplification product by using: a probe consisting of SEQ ID NO: 3 or a sequence that hybridizes, under conditions suitable for a polymerase chain reaction, with: SEQ ID NO: 7; or a sequence complementary thereto, wherein a fluorophore is attached to the 5' end of the probe, wherein at least one phosphate group is attached to the 3' end of the probe, and wherein a dark quencher is attached to the "T" residue of the probe, under conditions suitable for a polymerase chain reaction, whereby the presence of *Streptococcus pneumoniae* nucleic acid is detected, wherein the detection of *Streptococcus pneumoniae* nucleic acid diagnoses *Streptococcus pneumoniae* infection.

The disclosed compositions can also be used in a method for detecting *Streptococcus pneumoniae* nucleic acid in a biological sample, comprising: producing an amplification product by amplifying an *Streptococcus pneumoniae* nucleotide sequence using a sense primer and a antisense primer, wherein said primers are chosen from oligonucleotides that hybridize, under conditions suitable for a polymerase chain reaction, with a sequence of the psaA gene of *Streptococcus pneumoniae*; and detecting said amplification product, whereby the presence of *Streptococcus pneumoniae* nucleic acid is detected, wherein the sense primer consists of SEQ ID NO: 1 or a sequence that hybridizes, under conditions suitable for a polymerase chain reaction, with: SEQ ID NO: 5; or a sequence complementary thereto, wherein the detection of *Streptococcus pneumoniae* nucleic acid diagnoses *Streptococcus pneumoniae* infection.

The disclosed compositions can also be used in a method for detecting *Streptococcus pneumoniae* nucleic acid in a biological sample, comprising: producing an amplification product by amplifying an *Streptococcus pneumoniae* nucleotide sequence by real-time PCR using sense primers and antisense primers, wherein said primers are chosen from oligonucleotides that hybridize, under conditions suitable for a polymerase chain reaction, with a sequence of the psaA gene of *Streptococcus pneumoniae*; and detecting said amplification product, whereby the presence of *Streptococcus pneumoniae* nucleic acid is detected, wherein the antisense primer consists of SEQ ID NO: 2 or a sequence that hybridizes, under conditions suitable for a polymerase chain reaction, with: SEQ ID NO: 6; or a sequence complementary thereto, wherein the detection of *Streptococcus pneumoniae* nucleic acid diagnoses *Streptococcus pneumoniae* infection.

The disclosed compositions can also be used in a method for detecting *Streptococcus pneumoniae* nucleic acid in a biological sample using Real-Time PCR, comprising: producing an amplification product by amplifying an *Streptococcus pneumoniae* nucleotide sequence using sense primers and antisense primers, wherein said primers are chosen from oligonucleotides that hybridize, under conditions suitable for a polymerase chain reaction, with a sequence of the psaA gene of *Streptococcus pneumoniae*; and detecting said amplification product, whereby the presence of *Streptococcus pneumoniae* nucleic acid is detected, wherein the nondegenerate probe consists of SEQ ID NO: 3 or a sequence that hybridizes, under conditions suitable for a polymerase chain reaction, with: SEQ ID NO: 7; or a sequence complementary thereto, wherein a fluorophore is attached to the 5' end of the probe, wherein at least one phosphate group is attached to the 3' end of the probe, and wherein a dark quencher is attached to the "T" residue of the probe, wherein the detection of *Streptococcus pneumoniae* nucleic acid diagnoses *Streptococcus pneumoniae* infection.

The disclosed compositions can also be used in a method for detecting *Streptococcus pneumoniae* nucleic acid in a biological sample, comprising: producing an amplification product by amplifying an *Streptococcus pneumoniae* nucleotide sequence by real-time PCR using: a primer consisting of SEQ ID NO: 1 or a sequence that hybridizes, under conditions suitable for a polymerase chain reaction, with: SEQ ID NO: 5; or a sequence complementary thereto, and a primer consisting of SEQ ID NO: 2 or a sequence that hybridizes, under conditions suitable for a polymerase chain reaction, with: SEQ ID NO: 6; or a sequence complementary thereto, under conditions suitable for a polymerase chain reaction; and detecting said amplification product by using: a probe consisting of SEQ ID NO: 3 or a sequence that hybridizes, under conditions suitable for a polymerase chain reaction, with: SEQ ID NO: 7; or a sequence complementary thereto, wherein a fluorophore is attached to the 5' end of the probe, wherein at least one phosphate group is attached to the 3' end of the probe, and wherein a dark quencher is attached to the "T" residue of the probe, that hybridizes, under conditions suitable for a polymerase chain reaction, whereby the presence of *Streptococcus pneumoniae* nucleic acid is detected.

The disclosed compositions, either alone or in combination, can also be used to diagnose pneumococcal *pneumoniae*, by detecting the presence of the psaA gene in true *Streptococcus pneumoniae* species. True *Streptococcus pneumoniae* species are described elsewhere herein.

The disclosed compositions, either alone or in combination, can also be used to diagnose pneumococcal *pneumoniae*, by detecting the presence of the psaA gene in true *Streptococcus pneumoniae* species in different serotypes.

The disclosed compositions, either alone or in combination, can also be used to differentially diagnose true *Streptococcus pneumoniae* infection from Pneumococcus-like viridian streptococci species infections.

3. Methods of Evaluating Expression of the Gene Using Micro Arrays

The disclosed compositions, either alone or in combination, can be used as discussed herein as either reagents in micro arrays or as reagents to probe or analyze existing microarrays.

4. Methods of Screening Assay Using a Chip/Micro Array

The disclosed compositions, either alone or in combination, can be used as discussed herein as either reagents in chips and micro arrays or as reagents to probe or analyze existing chips and microarrays.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Detection of the psaA Gene of *Streptococcus pneumoniae* a) Methods
(1) Primers and Probes
Primers were designed and evaluated for their ability to amplify the psaA gene of *Streptooccus pneumoniae*:

```
                                          (SEQ ID NO:1)
1F: 5'GCCCTAATAAATTGGAGGATCTAATGA3'

(SEQ ID NO: 2)
1R: 5'GACCAGAAGTTGTATCTTTTTTCCG3'

(SEQ ID NO: 8)
2F: 5'GCCCTAATAAATTGGAGGATCTAATGA3'

(SEQ ID NO: 9)
2R: 5'TTGACCAGAAGTTGTATCTTTTTTCC3'

(SEQ ID NO: 10)
3F: 5'CCCTAATAAATTGGAGGATCTAATGAAA3'

(SEQ ID NO: 11)
3R: 5'CAACTTTTAGTTTTGACCAGAAGTTGTA3'
```

The primers were evaluated by testing the ability of different combinations of the primers to amplify the psaA gene of *Streptooccus pneumoniae* DNA.

Two different probes were designed and evaluated for their ability to bind the psaA gene of *Streptooccus pneumoniae*:
Probe 1: 5' (X)-TTTCTTTCTGCAA"T"CATTCTTGTAG-CATGTGCTAGC-(Y) 3', where X is a FAM, Y is a phosphate group, and ROX is attached to the "T".
Probe 2: 5' (X) CTAGCACATGC"T"ACAAGAATGATTG-CAGAAAGAAA-(Y) 3', where X is a HEX, Y is a phosphate group, and ROX is attached to the "T".
The nucleotide sequence of Probe 2 (SEQ ID NO: 3) was designed by changing the nucleotide sequence of Probe 1 (SEQ ID NO: 7) to the reverse complement and subtracting the last nucleotide in the 3' end.

The probes were evaluated by testing the ability to bind the psaA gene of *Streptooccus pneumoniae*.

Combinations of the primers and probes were also assayed for their ability to detect the psaA gene of *Streptooccus pneumoniae* in a real-time PCR reaction by combining one forward and one reverse primer listed above with one of the two probes listed above.

(2) *Streptococcus pneumoniae* (Spn) and Pneumococcus-like Viridians Streptococci Species (P-LVS) Isolates Isolates were obtained from the Streptococcal Reference laboratory. The isolates tested consisted of: 40 Spn (28 different serotypes); 4 non-encapsulated Spn (representative of conjunctivitis outbreaks); 51 P-LVS (*S. pseudopneumoniae, S. mitis, S. oralis, S. sanguinis, S. parasanguinis, S. peroris, S. infantis, S. gordonii, S. cristatus, S. salivarius, S. vestibularis, S. australis, S. sinensis, S. oligofermentans, S. intestinalis*); other upper respiratory organisms such as *S. pyogenes, S. agalactiae, Staphylococcus aureus, Dolosigranulum pigrum, Enterococcus faecalis*, and *Escherichia coli*.

The strains were identified and characterized by optochin susceptibility, bile solubility and Accuprobe [GENE-PROBE] tests, and stored in defibrinated sheep blood at −70° C.

(3) DNA Extraction

Bacterial DNA was extracted from the isolates using the DNeasy Tissue Kit (QIAGEN GmbH).

The samples were prepared by harvesting the cells (maximum $2\times10^9$ cells) in a microcentrifuge tube by centrifugation for 10 min at 5000×g (7500 rpm) and then discarding the supernatant. The bacterial pellet was then resuspended in 180 µl of lysis buffer containing 0.02 g/ml of lysozyme (Sigma) and 5 U/ml of mutanolysin (Sigma) for 1 hour at 37° C.

25 µl of proteinase K and 200 µl of Buffer AL were added to the samples and the samples were mixed by vortexing. The samples were then incubated at 70° C. for 30 min. Then 200 µl of ethanol (96-100%) were added to the samples. The samples were then mixed thoroughly by vortexing. The mixture was then transferred into the DNeasy Mini spin column placed in a 2 ml collection tube. The sample was then centrifuged at ≧6000×g (8000 rpm) for 1 min. The flow-through and collection tube were then discarded and the DNeasy Mini spin column was placed in a new 2 ml collection tube and 500 µl of Buffer AW1 was added. The new mixture was centrifuged for 1 min at ≧6000×g (8000 rpm) for 1 min. Again the flow-through and collection tube were then discarded and the DNeasy Mini spin column was placed in a new 2 ml collection tube. 500 µl of Buffer AW2 was added to the sample and centrifuged for 3 min at 20,000×g (14,000 rpm) to dry the DNeasy membrane. After centrifugation, the flow-through and collection tube were then discarded. The DNeasy Mini spin column was the placed in a new 2 ml microcentrifuge tube and 200 µl Buffer AE was added directly onto the DNeasy membrane and the sample was incubated at room temperature for 1 min and then centrifuged for 1 min at ≧6000×g (8000 rpm) for 1 min to elute the sample. The elution step was then repeated.

The nucleic acids were conserved at 4° C. until the PCR step.

(4) PCR Reaction

The PCR conditions used were as follows: 500 nM primers, 100 nM probe, 1× TaqMan™ universal PCR master mix buffer, and 2.5 µl of DNA in a total volume of 25 µl. No template controls were prepared adding 2.5 µl volume of sterile water instead DNA. No template controls were prepared adding 2.5 µl volume of sterile water instead of DNA.

Figure 3:
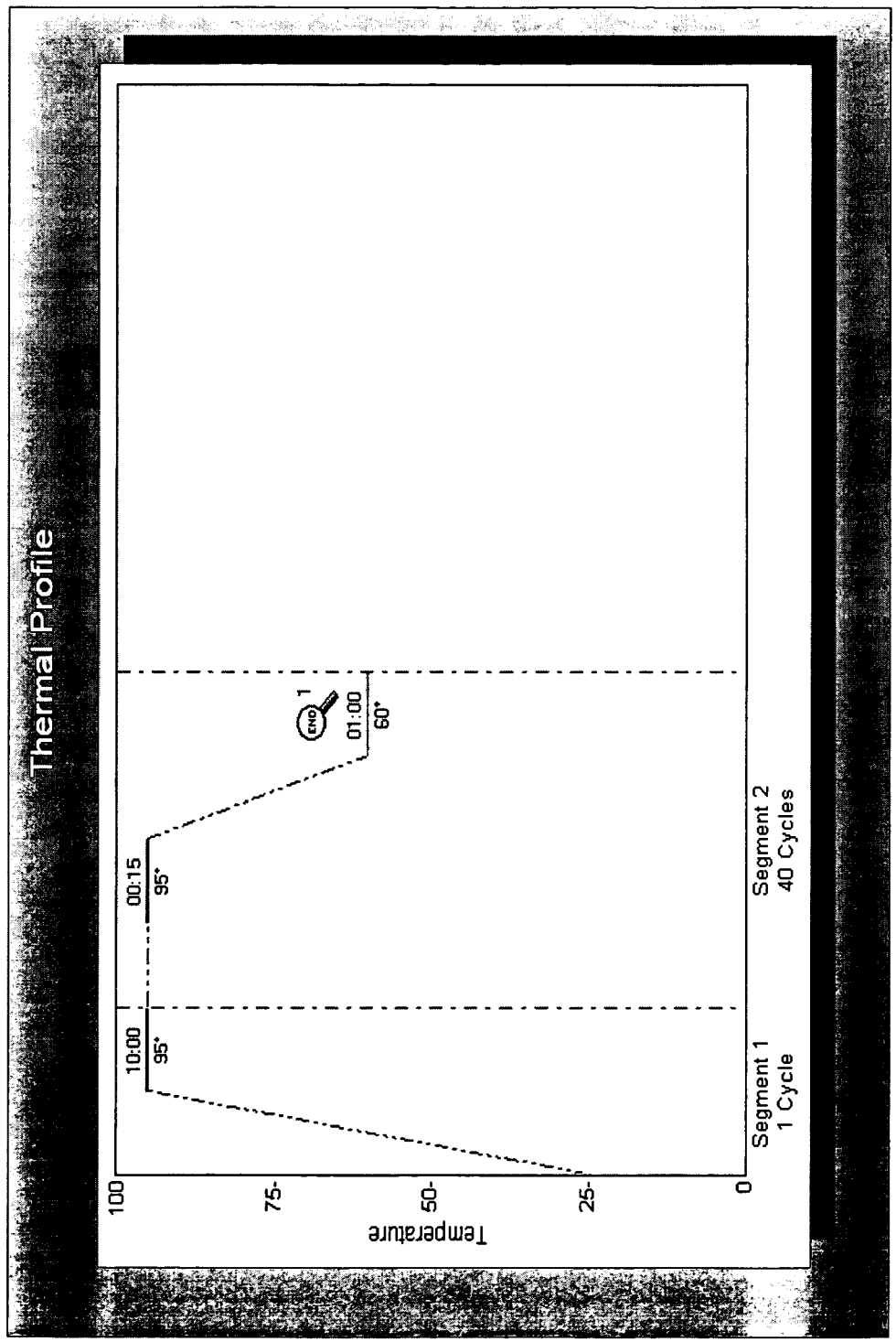
FIG. 3 shows the thermal profile of the real-time PCR method used to detect the psaA gene of *Streptococcus pneumoniae*

Cycling conditions used were as follows: one cycle of denaturation at 95° C. for 10 min followed by 40 cycles of denaturation at 95° C. for 15 s and amplicon extension at 60° C. for 60 seconds. (See FIG. 3 showing Thermal Profile Setup).

(5) Machine and Quantification

Optimization of the primers was carried out using gradient melt temperature tests using SYBR green in an iCycler format (BIO-RAD).

The probe was tested in a quantitative PCR system using the MX3000P format (Stratagene)

All the real-time PCR reactions were carried out with the aid of the MX3000P machine (Stratagene), which machine detected the signal with the aid of a fluorescent probe (TaqMan™ probe) during the PCR cycles.

The MX3000P system is a thermocycler, in which each well (n=96) was connected to an optical fiber, this optical fiber was connected to a laser. A CCD camera collected the fluorescent emissions about every 6 seconds for each well. The MX3000P software analyzed the fluorescent data and determined the number of target copies in a sample.

The quantification was based on the principle of real-time PCR. Specifically, the PCR product was characterized during the PCR cycle at the moment at which the amplification was detectable by the degradation of the probe which was linked to the accumulation of PCR products. (See FIGS. 4 and 5). The higher the number of starting target copies, the fewer PCR cycles that were required in order to detect a significant increase in fluorescence Real-time PCR data were quantified in terms of cycle threshold ($C_t$) values. Ct values are inversely related to the amount of starting template; high $C_t$ values correlate with low copy numbers of the psaA gene, whereas low $C_t$ values correlate with high levels of the psaA gene.

Figure 4:
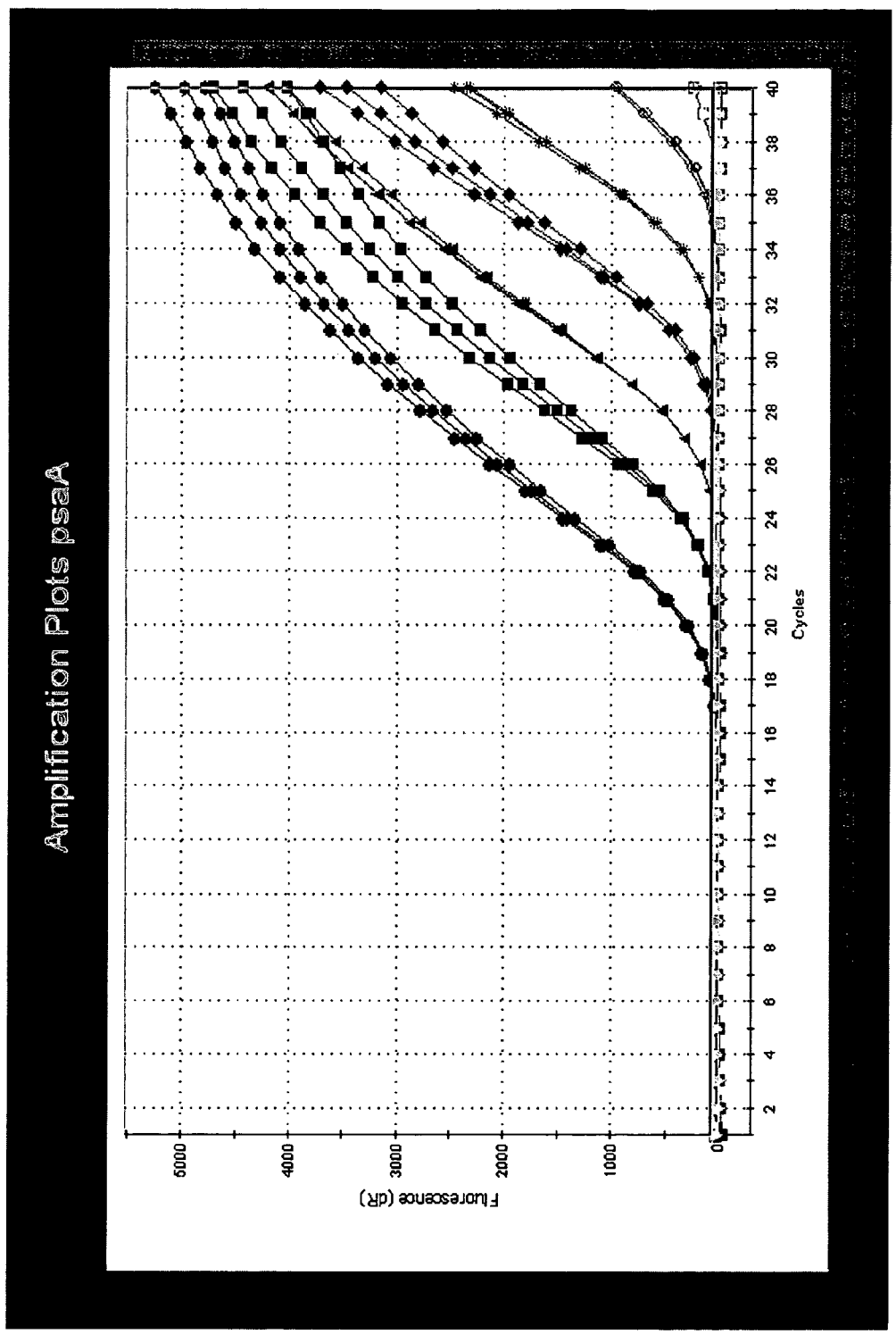
FIG. 4 shows the dilution/concentration curve of Amplification Plots psaA Strain ATCC 33400T *S. pneumoniae.*
Figure 5:
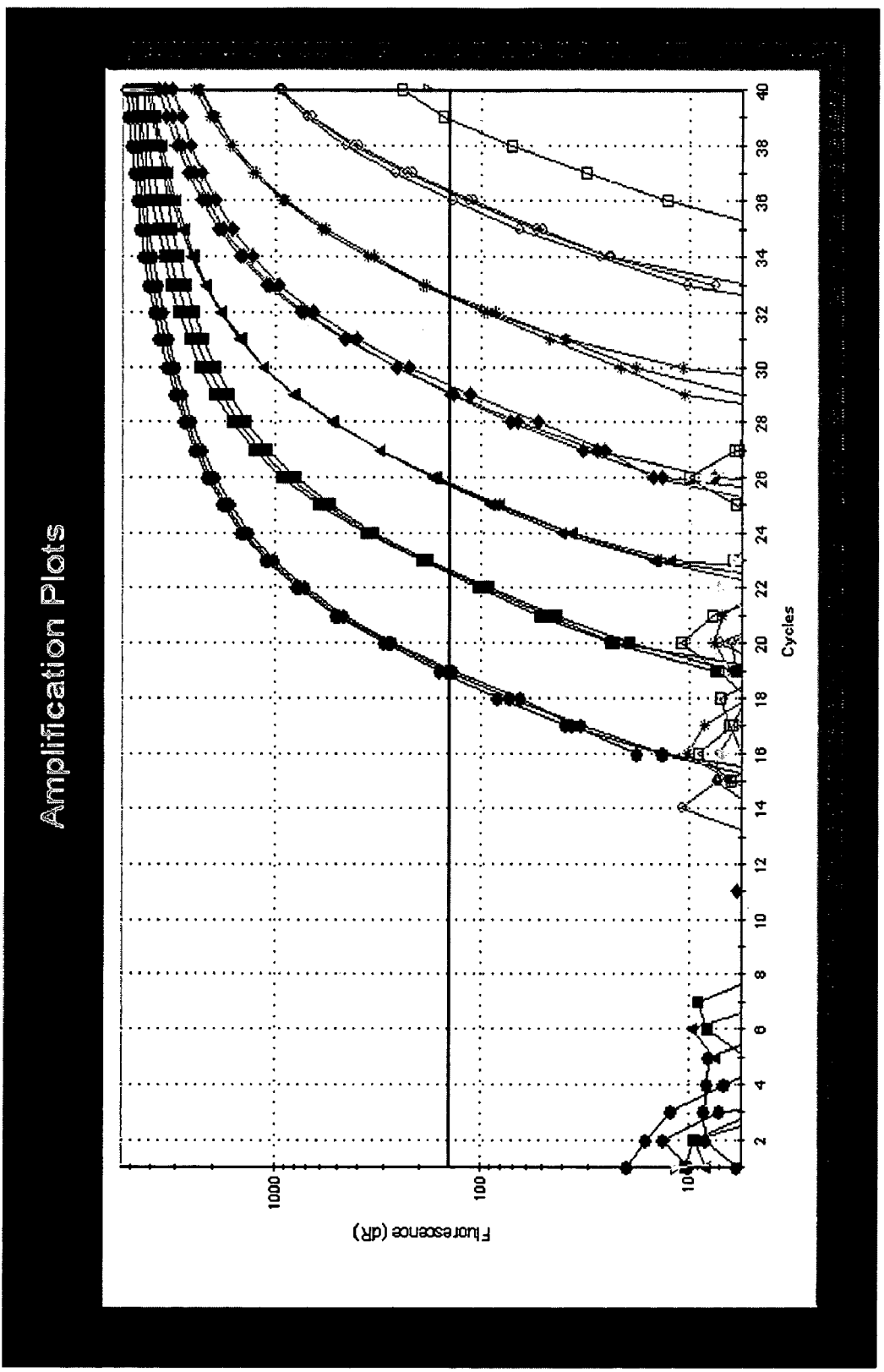
FIG. 5 shows amplification plots for the psaA Strain ATCC 33400T of *S. pneumoniae.*

The number of target copies in a sample was quantified measuring the Ct value, and using a standard curve (FIGS. 4 and 5). In theory, if the PCR functions at 100%, 3.32 cycles were required for each 10-fold increase of targets.

The second parameter (ΔRn) was used to confirm that the PCR signal was positive. The ΔRn was the difference in the fluorescence detected between the measured fluorescence of the background noise and the detected fluorescence of the sample to be analyzed.

b) Results

The first set of primers (1F and 1R; SEQ ID NOS: 1 and 2, respectively) specifically and sensitively identified the psaA gene of Sterpotoccus pneumoniae. under the gradient melt temperature tests using SYBR green in an iCycler format (BIO-RAD).

After the optimization of the primers, the probe was tested in a quantitative PCR system using MX3000P format (Stratagene).

2. Example 2

Specificity of Method

Accurate pneumococcal disease diagnosis has been frequently hampered not only by the difficulties in obtaining isolates of the organism from patient specimens, but also by the misidentification of Pneumococcus-like viridans streptococci species (P-LVS) as *Streptococcus pneumoniae* (Spn). This is especially critical when the considered specimen comes from respiratory site.

Here, three real time PCR assays designed for detection of specific sequence regions of psaA, lytA and ply genes not similar to published PCR procedures were developed; two other assays for lytA and ply developed previously (McAlvin et al. and Corless et al., respectively) were also evaluated.

a) Methods (1) Primers and Probes

The primers and probes specific to psaA were identified as described in Example 1.

The primers used in the real-time PCR reaction to detect the psaA gene of *Streptococcus pneumoniae* contained the following sequences:

```
                                        (SEQ ID NO: 1)
1F: 5'GCCCTAATAAATTGGAGGATCTAATGA3'

(SEQ ID NO: 2)
1R: 5'GACCAGAAGTTGTATCTTTTTTTCCG3'
```

The probe used in the real-time PCR reaction to detect the psaA gene of *Streptococcus pneumoniae* had the sequence:
Probe 2: 5' (X) CTAGCACATGC"T"ACAAGAATGATTG-CAGAAAGAAA-(Y) 3', where X is a HEX, Y is a phosphate group, and ROX is attached to the "T".

In addition to the primer and probe sequences for ply and lytA generated for this study, primers and probes for these two genes were also generated to match the sequences of the primers and probes for lytA and ply as described previously (McAlvin et al. and Corless et al., respectively) and are hereby incorporated by reference.

(2) *Streptococcus pneumoniae* (Spn) and Pneumococcus-like viridians Streptococci Species (P-LVS) Isolates Isolates were obtained from the Streptococcal Reference laboratory. The isolates tested consisted of: 40 Spn (28 different serotypes); 4 non-encapsulated Spn (representative of conjunctivitis outbreaks); 51 P-LVS (*S. pseudopneumoniae, S. mitis, S. oralis, S. sanguinis, S. parasanguinis, S. peroris, S. infantis, S. gordonii, S. cristatus, S. salivarius, S. vestibularis, S. australis, S. sinensis, S. oligofermentans, S. intestinalis*); other upper respiratory organisms such as *S. pyogenes, S. agalactiae, Staphylococcus aureus, Dolosigranulum pigrum, Enterococcus faecalis*, and *Escherichia coli*.

The strains were identified and characterized by optochin susceptibility, bile solubility and Accuprobe [GENE-PROBE] tests, and stored in defibrinated sheep blood at −70° C.

All P-LVS isolates were confirmed as non-Spn by DNA/DNA reassociation.

(3) DNA Extraction

Bacterial DNA was extracted from the isolates using the DNeasy Tissue Kit (Qiagen).

The samples were prepared by harvesting the cells (maximum 2×10⁹ cells) in a microcentrifuge tube by centrifugation for 10 min at 5000×g (7500 rpm) and then discarding the supernatant. The bacterial pellet was then resuspended in 180 μl of lysis buffer containing 0.02 g/ml of lysozyme (Sigma) and 5 U/ml of mutanolysin (Sigma) for 1 hour at 37° C.

25 μl of proteinase K and 200 μl of Buffer AL were added to the samples and the samples were mixed by vortexing. The samples were then incubated at 70° C. for 30 min. Then 200 μl of ethanol (96-100%) were added to the samples. The samples were then mixed thoroughly by vortexing. The mixture was then transferred into the DNeasy Mini spin column placed in a 2 ml collection tube. The sample was then centrifuged at ≧6000×g (8000 rpm) for 1 min. The flow-through and collection tube were then discarded and the DNeasy Mini spin column was placed in a new 2 ml collection tube and 500 μl of Buffer AW1 was added. The new mixture was centrifuged for 1 min at ≧6000×g (8000 rpm) for 1 min. Again the flow-through and collection tube were then discarded and the DNeasy Mini spin column was placed in a new 2 ml collection tube. 500 µl of Buffer AW2 was added to the sample and centrifuged for 3 min at 20,000×g (14,000 rpm) to dry the DNeasy membrane. After centrifugation, the flow-through and collection tube were then discarded. The DNeasy Mini spin column was the placed in a new 2 ml microcentrifuge tube and 200 µl Buffer AE was added directly onto the DNeasy membrane and the sample was incubated at room temperature for 1 min and then centrifuged for 1 min at ≧6000×g (8000 rpm) for 1 min to elute the sample. The elution step was then repeated.

The nucleic acids were conserved at 4° C. until the PCR step as described in Example/above.

(4) PCR Reaction

The PCR conditions used were as follows: 500 nM primers, 100 nM probe, 1× TaqMan™ universal PCR master mix buffer, and 2.5 µl of DNA in a total volume of 25 µl. No template controls were prepared adding 2.5 µl volume of sterile water instead DNA. No template controls were prepared adding 2.5 µl volume of sterile water instead of DNA. Cycling conditions used were as follows: one cycle of denaturation at 95° C. for 10 min followed by 40 cycles of denaturation at 95° C. for 15 s and amplicon extension at 60° C. for 60 seconds. (See FIG. 3).

(5) Machine and Quantification

All the real-time PCR reactions were carried out with the aid of the MX3000P machine (Stratagene), which machine detected the signal with the aid of a fluorescent probe (TaqMan™ probe) during the PCR cycles.

The MX3000P system is a thermocycler, in which each well (n=96) was connected to an optical fiber, this optical fiber was connected to a laser. A CCD camera collected the fluorescent emissions about every 6 seconds for each well. The MX3000P software analyzed the fluorescent data and determined the number of target copies in a sample.

The quantification was based on the principle of real-time PCR. Specifically, the PCR product was characterized during the PCR cycle at the moment at which the amplification was detectable by the degradation of the probe which was linked to the accumulation of PCR products. (See FIGS. 4 and 5). The higher the number of starting target copies, the fewer PCR cycles that were required in order to detect a significant increase in fluorescence.

Real-time RT-PCR data were quantified in terms of cycle threshold ($C_t$) values. Ct values are inversely related to the amount of starting template; high $C_t$ values correlate with low levels of gene expression, whereas low $C_t$ values correlate with high levels of gene expression.

The number of target copies in a sample was quantified measuring the Ct value, and using a standard curve (FIGS. 4 and 5). In theory, if the PCR functions at 100%, 3.32 cycles were required for each 10-fold increase of targets.

The second parameter (Delta Rn) was used to confirm that the PCR signal was positive. The delta Rn was the difference in the fluorescence detected between the measure fluorescence of the background noise and the detected fluorescence of the sample to be analyzed.

b) Results

All five assays tested were positive for all Spn isolates, and were able to detect less than 15 copies of DNA. The newly developed assays targeting psaA and lytA were negative for all non-Spn isolates except one *S. pseudopneumoniae* isolate that was positive for psaA assay. The same isolate was undefined for lytA PCR assay previously developed by McAlvin.

Both ply PCRs were positive for all isolates of *S. pseudopneumoniae* along with 12 other isolates of P-LVS. Thus, the use of ply gene for pneumococcal detection can lead to misidentification of P-LVS. The new assays for psaA and lytA were more specific for detection of true Spn than the assays developed by McAlvin et al. and Corless et al.

F. REFERENCES

Abravaya, K., Huff, J., Marshall, R., Merchant, B., Mullen, C., Schneider, G. & Robinson, J. (2003) Molecular beacons as diagnostic tools: technology and applications. *Clin Chem Lab Med*, 41, 468-474.

Adler, M., Wacker, R. & Niemeyer, C. M. (2003) A real-time immuno-PCR assay for routine ultrasensitive quantification of proteins. *Biochem Biophys Res Commun*, 308, 240-250.

Aerts, J. L., Gonzales, M. I. & Topalian, S. L. (2004) Selection of appropriate control genes to assess expression of tumor antigens using real-time RT-PCR. *Biotechniques*, 36, 84-86, 88, 90-81.

Alizadeh, M., Bernard, M., Danic, B., Dauriac, C., Birebent, B., Lapart, C., Lamy, T., Le Prise, P. Y., Beauplet, A., Bories, D., Semana, G. & Quelvennec, E. (2002) Quantitative assessment of hematopoietic chimerism after bone marrow transplantation by real-time quantitative polymerase chain reaction. *Blood*, 99, 4618-4625.

Alonso, A., Martin, P., Albarran, C., Garcia, P., Garcia, O., de Simon, L. F., Garcia-Hirschfeld, J., Sancho, M., de La Rua, C. & Fernandez-Piqueras, J. (2004) Real-time PCR designs to estimate nuclear and mitochondrial DNA copy number in forensic and ancient DNA studies. *Forensic Sci Int*, 139, 141-149.

Barletta, J. M., Edelman, D. C. & Constantine, N. T. (2004) Lowering the detection limits of HIV-1 viral load using real-time immuno-PCR for HIV-1 p24 antigen. *Am J Clin Pathol*, 122, 20-27.

Barrois, M., Bieche, I., Mazoyer, S., Champeme, M. H., Bressac-de Paillerets, B. & Lidereau, R. (2004) Real-time PCR-based gene dosage assay for detecting BRCA1 rearrangements in breast-ovarian cancer families. *Clin Genet*, 65, 131-136.

Bennett, C. D., Campbell, M. N., Cook, C. J., Eyre, D. J., Nay, L. M., Nielsen, D. R., Rasmussen, R. P. & Bernard, P. S. (2003) The LightTyper: high-throughput genotyping using fluorescent melting curve analysis. *Biotechniques*, 34, 1288-1292, 1294-1285.

Bernard, P. S., Ajioka, R. S., Kushner, J. P. & Wittwer, C. T. (1998) Homogeneous multiplex genotyping of hemochromatosis mutations with fluorescent hybridization probes. *Am J Pathol*, 153, 1055-1061.

Berry, A. M., R. A. Lock, D. Hansman, and J. C. Paton. 1989. Contribution of autolysin to virulence of *Streptococcus pneumoniae*. Infect. Immun. 57: 2324-2330.

Bieche, I., Olivi, M., Champeme, M. H., Vidaud, D., Lidereau, R. & Vidaud, M. (1998) Novel approach to quantitative polymerase chain reaction using real-time detection: application to the detection of gene amplification in breast cancer. *Int J Cancer*, 78, 661-666.

Bischoff, F. Z., Marquez-Do, D. A., Martinez, D. I., Dang, D., Home, C., Lewis, D. & Simpson, J. L. (2003) Intact fetal cell isolation from maternal blood: improved isolation using a simple whole blood progenitor cell enrichment approach (RosetteSep). *Clin Genet*, 63, 483-489.

Bischoff, F. Z., Sinacori, M. K., Dang, D. D., Marquez-Do, D., Home, C., Lewis, D. E. & Simpson, J. L. (2002) Cell-free fetal DNA and intact fetal cells in maternal blood circulation: implications for first and second trimester non-invasive prenatal diagnosis. *Hum Reprod Update*, 8, 493-500.

Blakely, W. F., Miller, A. C., Luo, L., Lukas, J., Homby, Z. D., Hamel, C. J., Nelson, J. T., Escalada, N. E. & Prasanna, P. G. (2002) Nucleic acid molecular biomarkers for diagnostic biodosimetry applications: use of the fluorogenic 5'-nuclease polymerase chain reaction assay. *Mil Med*, 167, 16-19.

Blakely, W. F., Prasanna, P. G., Grace, M. B. & Miller, A. C. (2001) Radiation exposure assessment using cytological and molecular biomarkers. *Radiat Prot Dosimetry*, 97, 17-23.

Bremer, C., Tung, C. H. & Weissleder, R. (2002) Molecular imaging of MMP expression and therapeutic MMP inhibition. *Acad Radiol*, 9 Suppl 2, S314-315.

Brennan, R. E. & Samuel, J. E. (2003) Evaluation of Coxiella burnetii antibiotic susceptibilities by real-time PCR assay. *J Clin Microbiol*, 41, 1869-1874.

Brown, P. D., and S. A. Lerner. 1998. Community-acquired pneumonia. Lancet 352:1295-1302.

Bryant, P. A., Li, H. Y., Zaia, A., Griffith, J., Hogg, G., Curtis, N. & Carapetis, J. R. (2004) Prospective study of a real-time PCR that is highly sensitive, specific, and clinically useful for diagnosis of meningococcal disease in children. *J Clin Microbiol*, 42, 2919-2925.

Burger, H., Foekens, J. A., Look, M. P., Meijer-van Gelder, M. E., Klijn, J. G., Wiemer, E. A., Stoter, G. & Nooter, K. (2003) RNA expression of breast cancer resistance protein, lung resistance-related protein, multidrug resistance-associated proteins 1 and 2, and multidrug resistance gene 1 in breast cancer: correlation with chemotherapeutic response. *Clin Cancer Res*, 9, 827-836.

Bustin, S. A. (2000) Absolute quantification of mRNA using real-time reverse transcription polymerase chain reaction assays. *J Mol Endocrinol*, 25, 169-193.

Bustin, S. A. (2002) Quantification of mRNA using real-time reverse transcription PCR (RT-PCR): trends and problems. *J Mol Endocrinol*, 29, 23-39.

Chen, X., Zehnbauer, B., Gnirke, A. & Kwok, P. Y. (1997) Fluorescence energy transfer detection as a homogeneous DNA diagnostic method. *Proc Natl Acad Sci USA*, 94, 10756-10761.

Cherian, T., M. K. Lalitha, A. Manoharan, K. Thomas, R. H. Yolken, and M. C. Steinhoff. 1998. PCR-enzyme immunoassay for detection of *Streptococcus pneumoniae* DNA in cerebrospinal fluid samples from patients with culture-negative meningitis. J. Clin. Microbiol. 36:3605-3608.

Cilloni, D., Gottardi, E., De Micheli, D., Serra, A., Volpe, G., Messa, F., Rege-Cambrin, G., Guerrasio, A., Divona, M., Lo Coco, F. & Saglio, G. (2002) Quantitative assessment of WT1 expression by real time quantitative PCR may be a useful tool for monitoring minimal residual disease in acute leukemia patients. *Leukemia*, 16, 2115-2121.

Cleary, T. J., Roudel, G., Casillas, O. & Miller, N. (2003) Rapid and specific detection of Mycobacterium tuberculosis by using the Smart Cycler instrument and a specific fluorogenic probe. *J Clin Microbiol*, 41, 4783-4786.

Corless C E, Guiver M, Borrow R, Edwards-Jones V, Fox A J, Kaczmarski E B. Simultaneous detection of *Neisseria meningitidis, Haemophilus influenzae,* and *Streptococcus pneumoniae* in suspected cases of meningitis and septicemia using real-time PCR. *J Clin Microbiol*. April 2001;39(4):1553-8.

Cottrell, S. E., Distler, J., Goodman, N. S., Mooney, S. H., Kluth, A., Olek, A., Schwope, I., Tetzner, R., Ziebarth, H. & Berlin, K. (2004) A real-time PCR assay for DNA-methylation using methylation-specific blockers. *Nucleic Acids Res*, 32, e10.

Coupry, I., Monnet, L., Attia, A. A., Taine, L., Lacombe, D. & Arveiler, B. (2004) Analysis of CBP (CREBBP) gene deletions in Rubinstein-Taybi syndrome patients using real-time quantitative PCR. *Hum Mutat*, 23, 278-284.

Covault, J., Abreu, C., Kranzler, H. & Oncken, C. (2003) Quantitative real-time PCR for gene dosage determinations in microdeletion genotypes. *Biotechniques*, 35, 594-596, 598.

de Kok, J. B., Roelofs, R. W., Giesendorf, B. A., Pennings, J. L., Waas, E. T., Feuth, T., Swinkels, D. W. & Span, P. N. (2004) Normalization of gene expression measurements in tumor tissues: comparison of 13 endogenous control genes. *Lab Invest*.

Dheda, K., Huggett, J. F., Bustin, S. A., Johnson, M. A., Rook, G. & Zumla, A. (2004) Validation of housekeeping genes for normalizing RNA expression in real-time PCR. *Biotechniques*, 37, 112-114, 116, 118-119.

Dietmaier, W. & Hofstadter, F. (2001) Detection of microsatellite instability by real time PCR and hybridization probe melting point analysis. *Lab Invest*, 81, 1453-1456.

Doem, G. V., A. B. Brueggemann, H. Huynh, and E. Wingert. 1999. Antimicrobial resistance with *Streptococcus pneumoniae* in the United States, 1997-98. Emerg. Infect. Dis. 5:757-765.

Donohoe, G. G., Laaksonen, M., Pulkki, K., Ronnemaa, T. & Kairisto, V. (2000) Rapid single-tube screening of the C282Y hemochromatosis mutation by real-time multiplex allele-specific PCR without fluorescent probes. *Clin Chem*, 46, 1540-1547.

du Plessis, M., A. M. Smith, and K. P. Klugman. 1999. Application of pbp1A PCR in identification of penicillin-resistant *Streptococcus pneumoniae*. J. Clin. Microbiol. 37:628-632.

du Plessis, M., A. M. Smith, and K. P. Klugman. 1998. Rapid detection of penicillin-resistant *Streptococcus pneumoniae* in cerebrospinal fluid by a seminested-PCR strategy. J. Clin. Microbiol. 36:453-457.

Elmaagacli, A. H. (2002) Real-time PCR for monitoring minimal residual disease and chimerism in patients after allogeneic transplantation. *Int J Hematol*, 76 Suppl 2, 204-205.

Foulds, I. V., Granacki, A., Xiao, C., Krull, U. J., Castle, A. & Horgen, P. A. (2002) Quantification of microcystin-producing cyanobacteria and *E. coli* in water by 5'-nuclease PCR. *J Appl Microbiol*, 93, 825-834.

Freeman, W. M., Walker, S. J. & Vrana, K. E. (1999) Quantitative RT-PCR: pitfalls and potential. *Biotechniques*, 26, 112-122, 124-115.

Gabert, J., Beillard, E., van der Velden, V. H., Bi, W., Grimwade, D., Pallisgaard, N., Barbany, G., Cazzaniga, G., Cayuela, J. M., Cave, H., Pane, F., Aerts, J. L., De Micheli, D., Thirion, X., Pradel, V., Gonzalez, M., Viehmann, S., Malec, M., Saglio, G. & van Dongen, J. J. (2003) Standardization and quality control studies of 'real-time' quantitative reverse transcriptase polymerase chain reaction detection of fusion gene transcripts for residual disease detection in leukemia—a Europe Against Cancer program. *Leukemia*, 17, 2318-2357.

Garcia, A., B. Roson, J. L. Perez, R. Verdaguer, J. Dorca, J. Carratala, A. Casanova, F. Manresa, and R. Gudiol. 1999.

Usefulness of PCR and antigen latex agglutination test samples obtained by transthoracic needle aspiration for diagnosis of pneumococcal pneumonia. J. Clin. Microbiol. 37:709-714.

Gibbs, P. J., Tan, L. C., Sadek, S. A. & Howell, W. M. (2003) Comparative evaluation of 'TaqMan' RT-PCR and RT-PCR ELISA for immunological monitoring of renal transplant recipients. *Transpl Immunol*, 11, 65-72.

Gibellini, D., Vitone, F., Gori, E., La Placa, M. & Re, M. C. (2004) Quantitative detection of human immunodeficiency virus type 1 (HIV-1) viral load by SYBR green real-time RT-PCR technique in HIV-1 seropositive patients. *J Virol Methods*, 115, 183-189.

Gillespie, S. H. 1999. The role of the molecular laboratory in the investigation of *Streptococcus pneumoniae* infections. Semin. Respiratory Infect. 14: 269-275.

Gillespie, S. H., T. D. McHugh, H. Ayres, A. Dickens, A. Efstratiou, and G. C. Whiting. 1997. Allelic variation in *Streptococcus pneumoniae* autolysin (Nacetyl muramoyl-L-alanine amidase). Infect. Inmun. 65:3936-3938.

Gillespie, S. H., C. Ullman, M. D. Smith, and V. Emery. 1994. Detection of *Streptococcus pneumoniae* in sputum samples by PCR. J. Clin. Microbiol. 32:1308-1311.

Ginzinger, D. G., Godfrey, T. E., Nigro, J., Moore, D. H., 2nd, Suzuki, S., Pallavicini, M. G., Gray, J. W. & Jensen, R. H. (2000) Measurement of DNA copy number at microsatellite loci using quantitative PCR analysis. *Cancer Res*, 60, 5405-5409.

Giulietti, A., Overbergh, L., Valckx, D., Decallonne, B., Bouillon, R. & Mathieu, C. (2001) An overview of real-time quantitative PCR: applications to quantify cytokine gene expression. *Methods*, 25, 386-401.

Goidin, D., Mamessier, A., Staquet, M. J., Schmitt, D. & Berthier-Vergnes, O. (2001) Ribosomal 18S RNA prevails over glyceraldehyde-3-phosphate dehydrogenase and beta-actin genes as internal standard for quantitative comparison of mRNA levels in invasive and noninvasive human melanoma cell subpopulations. *Anal Biochem*, 295, 17-21.

Grace, M. B., McLeland, C. B. & Blakely, W. F. (2002) Real-time quantitative RT-PCR assay of GADD45 gene expression changes as a biomarker for radiation biodosimetry. *Int J Radiat Biol*, 78, 1011-1021.

Grace, M. B., McLeland, C. B., Gagliardi, S. J., Smith, J. M., Jackson, W. E., 3rd & Blakely, W. F. (2003) Development and assessment of a quantitative reverse transcription-PCR assay for simultaneous measurement of four amplicons. *Clin Chem*, 49, 1467-1475.

Gupta, M., Song, P., Yates, C. R. & Meibohm, B. (2004) Real-time PCR-based genotyping assay for CXCR2 polymorphisms. *Clin Chim Acta*, 341, 93-100.

Guy, R. A., Payment, P., Krull, U. J. & Horgen, P. A. (2003) Real-time PCR for quantification of Giardia and Cryptosporidium in environmental water samples and sewage. *Appl Environ Microbiol*, 69, 5178-5185.

Hahn, S., Zhong, X. Y., Troeger, C., Burgemeister, R., Gloning, K. & Holzgreve, W. (2000) Current applications of single-cell PCR. *Cell Mol Life Sci*, 57, 96-105.

Hall, L. M. C. 1998. Application of molecular typing the epidemiology of *Streptococcus pneumoniae*. J. Clin. Pathol. 51:270-274.

Hall, L. M., B. Duke, and G. Urwin. 1995. An approach to the identification of the pathogens of bacterial meningitis by the polymerase chain reaction. Eur. J. Clin. Microbiol. Infect. Dis. 14:1090-1094.

Harries, L. W., Wickham, C. L., Evans, J. C., Rule, A., Joyner, M. V. & Ellard, S. (2004) Analysis of haematopoietic chimaerism by quantitative real-time polymerase chain reaction. *Bone Marrow Transplant*, (in press).

Hartshorn, C., Rice, J. E. & Wangh, L. J. (2002) Developmentally-regulated changes of Xist RNA levels in single preimplantation mouse embryos, as revealed by quantitative real-time PCR. *Mol Reprod Dev*, 61, 425-436.

Hassan-King, M., I. Baldeh, O. Secka, A. Falade, and B. Greenwood. 1994. Detection of *Streptococcus pneumoniae* DNA in blood cultures by PCR. J. Clin. Microbiol. 32:1721-1724.

Hazbon, M. H. & Alland, D. (2004) Hairpin primers for simplified single-nucleotide polymorphism analysis of Mycobacterium tuberculosis and other organisms. *J Clin Microbiol*, 42, 1236-1242.

He, L., Chinnery, P. F., Durham, S. E., Blakely, E. L., Wardell, T. M., Borthwick, G. M., Taylor, R. W. & Turnbull, D. M. (2002) Detection and quantification of mitochondrial DNA deletions in individual cells by real-time PCR. *Nucleic Acids Res*, 30, e68.

Heid, C. A., Stevens, J., Livak, K. J. & Williams, P. M. (1996) Real time quantitative PCR. *Genome Res*, 6, 986-994.

Hendolin, P. H., A. Markkanen, J. Ylikoski, and J. J. Wahlfors. 1997. Use of multiplex PCR for simultaneous detection of four bacterial species in middle ear effusions. J. Clin. Microbiol. 35:2854-2858.

Higuchi, R., Fockler, C., Dollinger, G. & Watson, R. (1993) Kinetic PCR analysis: real-time monitoring of DNA amplification reactions. *Biotechnology (NY)*, 11, 1026-1030.

Higuchi, R., Dollinger, G., Walsh, P. S. & Griffith, R. (1992) Simultaneous amplification and detection of specific DNA sequences. *Biotechnology (NY)*, 10, 413-417.

Higuchi, R. 1989. Simple and rapid preparation of samples for PCR, p. 31-38. In H. A. Erlich (ed.), PCR technology: principles and application for DNA amplification. Stockton Press, New York, N.Y.

Hiyoshi, M. & Hosoi, S. (1994) Assay of DNA denaturation by polymerase chain reaction-driven fluorescent label incorporation and fluorescence resonance energy transfer. *Anal Biochem*, 221, 306-311.

Holland, P. M., Abramson, R. D., Watson, R. & Gelfand, D. H. (1991) Detection of specific polymerase chain reaction product by utilizing the 5' - - - 3' exonuclease activity of Thermus aquaticus DNA polymerase. *Proc Natl Acad Sci USA*, 88, 7276-7280.

Hwa, H. L., Ko, T. M., Yen, M. L. & Chiang, Y. L. (2004) Fetal gender determination using real-time quantitative polymerase chain reaction analysis of maternal plasma. *J Formos Med Assoc*, 103, 364-368.

Irwin, M. H., R. J. Moffatt, and C. A. Pinkert. 1999. Identification of transgenic mice by PCR analysis of saliva. Nat. Biotechnol. 14:1146-1148.

Isaacman, D. J., Y. Zhang, E. A. Reynolds, and G. D. Ehrlich. 1998. Accuracy of a polymerase chain reaction-based assay for detection of pneumococcal bacteremia in children. Pediatrics 101:813-816.

Jacoby, G. A. 1996. Antimicrobial-resistant pathogens in the 1990s. Annu. Rev. Med. 47:169-179.

Kanavakis, E., Traeger-Synodinos, J., Vrettou, C., Maragoudaki, E., Tzetis, M. & Kattamis, C. (1997) Prenatal diagnosis of the thalassaemia syndromes by rapid DNA analytical methods. *Mol Hum Reprod*, 3, 523-528.

Kariyazono, H., Ohno, T., Ihara, K., Igarashi, H., Joh-o, K., Ishikawa, S. & Hara, T. (2001) Rapid detection of the 22q11.2 deletion with quantitative real-time PCR. *Mol Cell Probes*, 15, 71-73.

Kawamura, Y., R. A. Whiley, S. E. Shu, T. Ezaki, and J. M. Hardie. 1999. Genetic approaches to the identification of the mitis group within the genus *Streptococcus*. Microbiology 145:2605-2613.

Kearns, A. M., Graham, C., Burdess, D., Heatherington, J. & Freeman, R. (2002a) Rapid real-time PCR for determination of penicillin susceptibility in pneumococcal meningitis, including culture-negative cases. *J Clin Microbiol*, 40, 682-684.

Kearns, A. M., Guiver, M., James, V. & King, J. (2001b) Development and evaluation of a real-time quantitative PCR for the detection of human cytomegalovirus. *J Virol Methods*, 95, 121-131.

Kearns, A. M., Draper, B., Wipat, W., Turner, A. J., Wheeler, J., Freeman, R., Harwood, J., Gould, F. K. & Dark, J. H. (2001a) LightCycler-based quantitative PCR for detection of cytomegalovirus in blood, urine, and respiratory samples. *J Clin Microbiol*, 39, 2364-2365.

Kearns, A. M., Turner, A. J., Eltringham, G. J. & Freeman, R. (2002b) Rapid detection and quantification of CMV DNA in urine using LightCycler-based real-time PCR. *J Clin Virol*, 24, 131-134.

Kearns, A. M., R. Freeman, O. M. Murphy, P. R. Seiders, M. Steward, and J. Wheeler. 1999. Rapid PCR-based detection of *Streptococcus pneumoniae* DNA-in cerebrospinal fluid. J. Clin. Microbiol. 37:3434.

Kogure, T., Ueno, Y., Iwasaki, T. & Shimosegawa, T. (2004) The efficacy of the combination therapy of 5-fluorouracil, cisplatin and leucovorin for hepatocellular carcinoma and its predictable factors. *Cancer Chemother Pharmacol*, 53, 296-304.

Kraus, G., Cleary, T., Miller, N., Seivright, R., Young, A. K., Spruill, G. & Hnatyszyn, H. J. (2001) Rapid and specific detection of the Mycobacterium tuberculosis complex using fluorogenic probes and real-time PCR. *Mol Cell Probes*, 15, 375-383.

Lareu, M. V. & Ruiz-Ponte, C. (2004) Genotyping SNPs With the LightCycler. *Methods Mol Biol*, 297, 127-140.

Laurendeau, I., Bahuau, M., Vodovar, N., Larramendy, C., Olivi, M., Bieche, I., Vidaud, M. & Vidaud, D. (1999) TaqMan PCR-based gene dosage assay for predictive testing in individuals from a cancer family with INK4 locus haploinsufficiency. *Clin Chem*, 45, 982-986.

Lee, L. G., Connell, C. R. & Bloch, W. (1993) Allelic discrimination by nick-translation PCR with fluorogenic probes. *Nucleic Acids Res*, 21, 3761-3766.

Lee, L. G., Livak, K. J., Mullah, B., Graham, R. J., Vinayak, R. S. & Woudenberg, T. M. (1999) Seven-color, homogeneous detection of six PCR products. *Biotechniques*, 27, 342-349.

Lehmann, U. & Kreipe, H. (2004) Real-Time PCR-Based Assay for Quantitative Determination of Methylation Status. In: *Methods in Molecular Biology: Epigenetics Protocols*, Vol. 287, pp. 207-218. Humana Press.

Leruez-Ville, M., Minard, V., Lacaille, F., Buzyn, A., Abachin, E., Blanche, S., Freymuth, F. & Rouzioux, C. (2004) Real-time blood plasma polymerase chain reaction for management of disseminated adenovirus infection. *Clin Infect Dis*, 38, 45-52.

Liu, C. S., Tsai, C. S., Kuo, C. L., Chen, H. W., Lii, C. K., Ma, Y. S. & Wei, Y. H. (2003) Oxidative stress-related alteration of the copy number of mitochondrial DNA in human leukocytes. *Free Radic Res*, 37, 1307-1317.

Livak, K. J., Flood, S. J., Marmaro, J., Giusti, W. & Deetz, K. (1995) Oligonucleotides with fluorescent dyes at opposite ends provide a quenched probe system useful for detecting PCR product and nucleic acid hybridization. *PCR Methods Appl*, 4, 357-362.

Livak, K. J. & Schmittgen, T. D. (2001) Analysis of relative gene expression data using real-time quantitative PCR and the 2(-Delta Delta C(T)) Method. *Methods*, 25, 402-408.

Lovatt, A. (2002) Applications of quantitative PCR in the biosafety and genetic stability assessment of biotechnology products. *J Biotechnol*, 82, 279-300.

Lu, J.-J., C.-L. Permg, S.-Y. Lee, and C.-C. Wan. 2000. Use of PCR with universal primers and restriction endonuclease digestions for detection and identification of common bacterial pathogens in cerebrospinal fluid. J. Clin. Microbiol. 38:2076-2080.

Lyon, E. (2001) Mutation detection using fluorescent hybridization probes and melting curve analysis. *Expert Rev Mol Diagn*, 1, 92-101.

Mackay, I. M. (2004) Real-time PCR in the microbiology laboratory. *Clin Microbiol Infect*, 10, 190-212.

McAvin JC, Reilly P A, Roudabush R M, Barnes W J, Salmen A, Jackson G W, Beninga K K, Astorga A, McCleskey F K, Huff W B, Niemeyer D, Lohman K L. Sensitive and specific method for rapid identification of *Streptococcus pneumoniae* using real-time fluorescence PCR. *J. Clin Microbiol*. October 2001;39(10):3446-51.

Mengelle, C., Pasquier, C., Rostaing, L., Sandres-Saune, K., Puel, J., Berges, L., Righi, L., Bouquies, C. & Izopet, J. (2003) Quantitation of human cytomegalovirus in recipients of solid organ transplants by real-time quantitative PCR and pp65 antigenemia. *J Med Virol*, 69, 225-231.

Mhlanga, M. M. & Malmberg, L. (2001) Using molecular beacons to detect single-nucleotide polymorphisms with real-time PCR. *Methods*, 25, 463-471.

Mocellin, S., Rossi, C. R., Pilati, P., Nitti, D. & Marincola, F. M. (2003) Quantitative real-time PCR: a powerful ally in cancer research. *Trends Mol Med*, 9, 189-195.

Morrison, K. E., D. Lake, J. Crook, G. M. Carlone, E. Ades, R. Facklam, and J. S. Sampson. 2000. Confirmation ofpsaA in all 90 serotypes of *Streptococcus pneumoniae* by PCR and potential of this assay for identification and diagnosis. J. Clin. Microbiol. 38:434-437.

Morrison, T. B., Weis, J. J. & Wittwer, C. T. (1998) Quantification of low-copy transcripts by continuous SYBR Green I monitoring during amplification. *Biotechniques*, 24, 954-958, 960, 962.

Niesters, H. G. (2001) Quantitation of viral load using real-time amplification techniques. *Methods*, 25, 419-429.

Olive, D. M., and P. Bean. 1999. Principles and applications of methods for DNA-based typing of microbial organisms. J. Clin. Microbiol. 37:1661-1669.

O'Neill, A. M., S. H. Gillespie, and G. C. Whiting. 1999. Detection of penicillin susceptibility in *Streptococcus pneumoniae* by pbp2b PCR-restriction fragment length polymorphism analysis. J. Clin. Microbiol. 37:157-160.

Perandin, F., Manca, N., Calderaro, A., Piccolo, G., Galati, L., Ricci, L., Medici, M. C., Arcangeletti, M. C., Snounou, G., Dettori, G. & Chezzi, C. (2004) Development of a real-time PCR assay for detection of Plasmodium falciparum, Plasmodium vivax, and Plasmodium ovale for routine clinical diagnosis. *J Clin Microbiol*, 42, 1214-1219.

Pfaffl, M. W. (2001) A new mathematical model for relative quantification in real-time RT-PCR. *Nucleic Acids Res*, 29, e45.

Pozzi, G., M. R. Oggioni, and A. Tomasz. 1989. DNA probe for identification of *Streptococcus pneumoniae*. J. Clin. Microbiol. 27:370-372.

Raeymaekers, L. (2000) Basic principles of quantitative PCR. *Mol Biotechnol,* 15, 115-122.

Raja, S., El-Heffiawy, T., Kelly, L. A., Chestney, M. L., Luketich, J. D. & Godfrey, T. E. (2002) Temperature-controlled primer limit for multiplexing of rapid, quantitative reverse transcription-PCR assays: application to intraoperative cancer diagnostics. *Clin Chem,* 48, 1329-1337.

Rajeevan, M. S., Vernon, S. D., Taysavang, N. & Unger, E. R. (2001) Validation of array-based gene expression profiles by real-time (kinetic) RT-PCR. *J Mol Diagn,* 3, 26-31.

Read, S. J., Mitchell, J. L. & Fink, C. G. (2001) LightCycler multiplex PCR for the laboratory diagnosis of common viral infections of the central nervous system. *J Clin Microbiol,* 39, 3056-3059.

Rickert, A. M., Lehrach, H. & Sperling, S. (2004) Multiplexed real-time PCR using universal reporters. *Clin Chem,* 50, 1680-1683.

Ririe, K. M., Rasmussen, R. P. & Wittwer, C. T. (1997) Product differentiation by analysis of DNA melting curves during the polymerase chain reaction. *Anal Biochem,* 245, 154-160.

Rudolph, K. M., A. J. Parkinson, C. M. Black, and L. W. Mayer. 1993. Evaluation of polymerase chain reaction for diagnosis of pneumococcal pneumonia. J. Clin. Microbiol. 31:2661-2666.

Sabek, O., Dorak, M. T., Kotb, M., Gaber, A. O. & Gaber, L. (2002) Quantitative detection of T-cell activation markers by real-time PCR in renal transplant rejection and correlation with histopathologic evaluation. *Transplantation,* 74, 701-707.

Saha, B. K., Tian, B. & Bucy, R. P. (2001) Quantitation of HIV-1 by real-time PCR with a unique fluorogenic probe. *J Virol Methods,* 93, 33-42.

Salo, P., K. Laitinen, and M. Leinonen. 1999. Detection of pneumococcus from whole blood, buffy coat and serum samples by PCR during bacteremia in mice. APMIS 107: 601-605.

Salo, P., A. Ortqvist, and M. Leinonen. 1995. Diagnosis of bacteremic pneu-mococcal pneumonia by amplification of pneumolysin gene fragment in serum. J. Infect. Dis. 171: 479-482.

Sanchez, J. A., Pierce, K. E., Rice, J. E. & Wangh, L. J. (2004) Linear-after-the-exponential (LATE)-PCR: an advanced method of asymmetric PCR and its uses in quantitative real-time analysis. *Proc Natl Acad Sci USA,* 101, 1933-1938.

Sarris, A. H., Jiang, Y., Tsimberidou, A. M., Thomaides, A., Rassidakis, G. Z., Ford, R. J., Medeiros, L. J., Cabanillas, F. & McLaughlin, P. (2002) Quantitative real-time polymerase chain reaction for monitoring minimal residual disease in patients with advanced indolent lymphomas treated with rituximab, fludarabine, mitoxantrone, and dexamethasone. *Semin Oncol,* 29, 48-55.

Schmid, H., Cohen, C. D., Henger, A., Irrgang, S., Schlondorff, D. & Kretzler, M. (2003) Validation of endogenous controls for gene expression analysis in microdissected human renal biopsies. *Kidney Int,* 64, 356-360.

Siraj, A. K., Ozbek, U., Sazawal, S., Sirma, S., Timson, G., Al-Nasser, A., Bhargava, M., El Solh, H., Bhatia, K. & Gutierrez, M. I. (2002) Preclinical validation of a monochrome real-time multiplex assay for translocations in childhood acute lymphoblastic leukemia. *Clin Cancer Res,* 8, 3832-3840.

Smith, A. M., and K. P. Klugman. 1998. Alterations in PBP 1A essential for high-level penicillin resistance in *Streptococcus pneumoniae*. Antimicrob. Agents Chemother. 42:1329-1333.

Solinas, A., Brown, L. J., McKeen, C., Mellor, J. M., Nicol, J., Thelwell, N. & Brown, T. (2001) Duplex Scorpion primers in SNP analysis and FRET applications. *Nucleic Acids Res,* 29, E96.

Song, P., Li, S., Meibohm, B., Gaber, A. O., Honaker, M. R., Kotb, M. & Yates, C. R. (2002) Detection of MDR1 single nucleotide polymorphisms C3435T and G2677T using real-time polymerase chain reaction: MDR1 single nucleotide polymorphism genotyping assay. *AAPS Pharm Sci,* 4, E29.

Suzuki, T., Higgins, P. J. & Crawford, D. R. (2000) Control selection for RNA quantitation. *Biotechniques,* 29, 332-337.

Svanvik, N., Stahlberg, A., Sehlstedt, U., Sjoback, R. & Kubista, M. (2000) Detection of PCR products in real time using light-up probes. *Anal Biochem,* 287, 179-182.

Tan, W., Wang, K. & Drake, T. J. (2004) Molecular beacons. *Curr Opin Chem Biol,* 8, 547-553.

Tapp, I., Malmberg, L., Rennel, E., Wik, M. & Syvanen, A. C. (2000) Homogeneous scoring of single-nucleotide polymorphisms: comparison of the 5'-nuclease TaqMan assay and Molecular Beacon probes. *Biotechniques,* 28, 732-738.

Terry, C. F., Shanahan, D. J., Ballam, L. D., Harris, N., McDowell, D. G. & Parkes, H. C. (2002) Real-time detection of genetically modified soya using Lightcycler and ABI 7700 platforms with TaqMan, Scorpion, and SYBR Green I chemistries. *J AOAC Int,* 85, 938-944.

Thiede, C. (2004) Diagnostic chimerism analysis after allogeneic stem cell transplantation: new methods and markers. *Am J Pharmacogenomics,* 4, 177-187.

Thomassin, H., Kress, C. & Grange, T. (2004) MethylQuant: a sensitive method for quantifying methylation of specific cytosines within the genome. *Nucleic Acids Res,* 32, e168.

Toikka, P., S. Nikkari, O. Ruuskanen, M. Leinonen, and J. Mertsola. 1999. Pneumolysin PCR-based diagnosis of invasive pneumococcal infection in children. J. Clin. Microbiol. 37:633-637.

Torres, M. J., Criado, A., Ruiz, M., Llanos, A. C., Palomares, J. C. & Aznar, J. (2003) Improved real-time PCR for rapid detection of rifampin and isoniazid resistance in Mycobacterium tuberculosis clinical isolates. *Diagn Microbiol Infect Dis,* 45, 207-212.

Trinh, B. N., Long, T. I. & Laird, P. W. (2001) DNA methylation analysis by MethyLight technology. *Methods,* 25, 456-462.

Tung, C. H., Mahmood, U., Bredow, S. & Weissleder, R. (2000) In vivo imaging of proteolytic enzyme activity using a novel molecular reporter. *Cancer Res,* 60, 4953-4958.

Ubukata, K., Y. Asahi, A. Yamane, and M. Konno. 1996. Combinational detection of autolysin and penicillin-binding protein 2B genes of *Streptococcus pneumoniae* by PCR. J. Clin. Microbiol. 34:592-596.

Uhl, J. R., Bell, C. A., Sloan, L. M., Espy, M. J., Smith, T. F., Rosenblatt, J. E. & Cockerill, F. R., 3rd (2002) Application of rapid-cycle real-time polymerase chain reaction for the detection of microbial pathogens: the Mayo-Roche Rapid Anthrax Test. *Mayo Clin Proc,* 77, 673-680.

Van Belkum, A., M. Sluijter, R. De Groot, H. Verbrugh, and P. W. M. Hermans. 1996. Novel BOX repeat PCR assay for high-resolution typing of *Streptococcus pneumoniae* strains. J. Clin. Microbiol. 34:1176-1179.

van der Velden, V. H., Hochhaus, A., Cazzaniga, G., Szczepanski, T., Gabert, J. & van Dongen, J. J. (2003) Detection of minimal residual disease in hematologic malignancies by real-time quantitative PCR: principles, approaches, and laboratory aspects. *Leukemia*, 17, 1013-1034.

van Dijk, J. P., Heuver, L. H., van der Reijden, B. A., Raymakers, R. A., de Witte, T. & Jansen, J. H. (2002) A novel, essential control for clonality analysis with human androgen receptor gene polymerase chain reaction. *Am J Pathol*, 161, 807-812.

Vandesompele, J., De Preter, K., Pattyn, F., Poppe, B., Van Roy, N., De Paepe, A. & Speleman, F. (2002) Accurate normalization of real-time quantitative RT-PCR data by geometric averaging of multiple internal control genes. *Genome Biol*, 3, RESEARCH0034.

Vet, J. A., Majithia, A. R., Marras, S. A., Tyagi, S., Dube, S., Poiesz, B. J. & Kramer, F. R. (1999) Multiplex detection of four pathogenic retroviruses using molecular beacons. *Proc Natl Acad Sci USA*, 96, 6394-6399.

Vet, J. A. & Marras, S. A. (2005) Design and optimization of molecular beacon real-time polymerase chain reaction assays. *Methods Mol Biol*, 288, 273-290.

Vet, J. A., Van der Rijt, B. J. & Blom, H. J. (2002) Molecular beacons: colorful analysis of nucleic acids. *Expert Rev Mol Diagn*, 2, 77-86.

Von Ahsen, N., Armstrong, V. W. & Oellerich, M. (2004) Rapid, Long-Range Molecular Haplotyping of Thiopurine S-methyltransferase (TPMT) *3A, *3B, and *3C. *Clin Chem*.

Vrettou, C., Traeger-Synodinos, J., Tzetis, M., Malamis, G. & Kanavakis, E. (2003) Rapid screening of multiple beta-globin gene mutations by real-time PCR on the LightCycler: application to carrier screening and prenatal diagnosis of thalassemia syndromes. *Clin Chem*, 49, 769-776.

Vrettou, C., Traeger-Synodinos, J., Tzetis, M., Palmer, G., Sofocleous, C. & Kanavakis, E. (2004) Real-time PCR for single-cell genotyping in sickle cell and thalassemia syndromes as a rapid, accurate, reliable, and widely applicable protocol for preimplantation genetic diagnosis. *Hum Mutat*, 23, 513-521.

Wang, X. & Seed, B. (2003) A PCR primer bank for quantitative gene expression analysis. *Nucleic Acids Res*, 31, e154.

Waterfall, C. M. & Cobb, B. D. (2002) SNP genotyping using single-tube fluorescent bidirectional PCR. *Biotechniques*, 33, 80, 82-84, 86 passim.

Watson, D. A., V. Kapur, D. M. Musher, J. W. Jacobson, and J. M. Musser. 1995. Identification, cloning and sequencing of DNA essential for encapsulation of *Streptococcus pneumoniae*. Curr. Microbiol. 31:251-259.

Watzinger, F., Suda, M., Preuner, S., Baumgartinger, R., Ebner, K., Baskova, L., Niesters, H. G., Lawitschka, A. & Lion, T. (2004) Real-time quantitative PCR assays for detection and monitoring of pathogenic human viruses in immunosuppressed pediatric patients. *J Clin Microbiol*, 42, 5189-5198.

Whatmore, A. M., S. J. King, N. C. Doherty, D. Sturgeon, N. Chanter, and C. G. Dowson. 1999. Molecular characterization of equine isolates of *Streptococcus pneumoniae*: natural disruption of genes encoding the virulence factors pneumolysin and autolysin. Infect. Immun. 67:2776-2782.

Whatmore, A. M., and C. G. Dowson. 1999. The autolysin-encoding gene (lytA) of *Streptococcus pneumoniae* displays restricted allelic variation despite localized recombination events with genes of pneumococcal bacteriophage encoding cell wall lytic enzymes. Infect. lmrun. 67:4551-4556.

Whatmore, A. M., A. Efstratiou, A. P. Pickerill, K. Broughton, G. Woodard, D. Sturgeon, R. George, and C. G. Dowson. 2000. Genetic relationships between clinical isolates of *Streptococcus pneumoniae*, *Streptococcus oralis*, and *Streptococcus mitis*: characterization of "atypical" pneumococci and organisms allied to *S. mitis* harboring *S. pneumoniae* virulence factor-encoding genes. Infect. Immun. 68:1374-1382.

Wheeler, J., R. Freeman, M. Steward, K. Henderson, M. J. Lee, N. H. Piggott, G. J. Eltringham, and A. Galloway. 1999. Detection of pneumolysin in sputum. J. Med. Microbiol. 48:863-866.

Wittwer, C. T., Herrmann, M. G., Moss, A. A. & Rasmussen, R. P. (1997a) Continuous fluorescence monitoring of rapid cycle DNA amplification. *Biotechniques*, 22, 130-131, 134-138.

Wittwer, C. T., Reed, G. H., Gundry, C. N., Vandersteen, J. G. & Pryor, R. J. (2003) High-resolution genotyping by amplicon melting analysis using LCGreen. *Clin Chem*, 49, 853-860.

Wittwer, C. T., Ririe, K. M., Andrew, R. V., David, D. A., Gundry, R. A. & Balis, U. J. (1997b) The LightCycler: a microvolume multisample fluorimeter with rapid temperature control. *Biotechniques*, 22, 176-181.

Wittwer, C. T., M. G. Herrmann, A. A. Moss, and R. P. Rasmussen. 1997. Continuous fluorescence monitoring of rapid cycle DNA amplification. Bio-Techniques 22:130-138.

Wittwer, C. T., K. M. Ririe, R. V. Andrew, D. A. David, R. A. Gundry, and U. J. Balis. 1997. The Lightcycler™: a microvolume multisample fluorimeter with rapid temperature control. BioTechniques 22:176-181.

Zhang, Y., D. J. Isaacman, R. M. Wadowsky, J. Rydquist-White, J. C. Post, and G. D. Ehrlich. 1995. Detection of *Streptococcus pneumoniae* in whole blood by PCR. J. Clin. Microbiol. 33:596-601.

Zhou, L., Vandersteen, J., Wang, L., Fuller, T., Taylor, M., Palais, B. & Wittwer, C. T. (2004) High-resolution DNA melting curve analysis to establish HLA genotypic identity. *Tissue Antigens*, 64, 156-164.

Zimmermann, B., Holzgreve, W., Wenzel, F. & Hahn, S. (2002) Novel real-time quantitative PCR test for trisomy 21. *Clin Chem*, 48, 362-363.

G. Sequences

```
175. (psaA fwd primer)
                                          SEQ ID NO: 1
GCCCTAATAAATTGGAGGATCTAATGA 176. (psaA rev primer)
                                          SEQ ID NO: 2
GACCAGAAGTTGTATCTTTTTTTCCG 177. (psaA probe)
                                          SEQ ID NO: 3
CTAGCACATGCTACAAGAATGATTGCAGAAAGAAA 178. (psaA gene sequence)
                                          SEQ ID NO: 4
TACTGCTTCA GTTTTGGGAC TCTTTATTGG CTATAGTTTT
AATGTTGCGG CAGGTTCTAG TATCGTGCTT ACAGCTGCTA
GTTTCTTTCT CATTAGCTTC TTTATCGCTC CCAAACAACG
ATATTTGAAA CTGAAAAATA AACATTTGTT AAAATAAGGG
GCAAAGCCCT AATAAATTGG AGGATCTAAT GAAAAAATTA
GGTACATTAC TCGTTCTCTT TCTTTCTGCA ATCATTCTTG
TAGCATGTGC TAGCGGAAAA AAAGATACAA CTTCTGGTCA
AAAACTAAAA GTTGTTGCTA CAAACTCAAT CATCGCTGAT
ATTACTAAAA ATATTGCTGG TGACAAAATT GACCTTCATA
```

-continued

```
GTATCGTTCC GATTGGGCAA GACCCACACG AATACGAACC
ACTTCCTGAA GACGTTAAGA AAACTTCTGA GGCTGATTTG
ATTTTCTATA ACGGTATCAA CCTTGAAACA GGTGGCAATG
CTTGGTTTAC AAAATTGGTA GAAAATGCCA AGAAAACTGA
AAACAAAGAC TACTTCGCAG TCAGCGACGG CGTTGATGTT
ATCTACCTTG AAGGTCAAAA TGAAAAGGA AAAGAAGACC
CACACGCTTG GCTTAACCTT GAAAACGGTA TTATTTTTGC
TAAAATATC GCCAAACAAT TGAGCGCCAA AGACCCTAAC
AATAAAGAAT TCTATGAAAA AAATCTCAAA GAATATACTG
ATAAGTTAGA CAAACTTGAT AAAGAAAGTA AGGATAAATT
TAATAAGATC CCTGCTGAAA AGAAACTCAT TGTAACCAGC
GAAGGAGCAT TCAAATACTT CTCTAAAGCC TATGGTGTCC
CAAGTGCCTA CATCTGGGAA ATCAATACTG AAGAAGAAGG
AACTCCTGAA CAAATCAAGA CCTTGGTTGA AAAACTTCGC
CAAACAAAAG TTCCATCACT CTTTGTAGAA TCAAGTGTGG
ATGACCGTCC AATGAAAACT GTTTCTCAAG ACACAAACAT
CCCAATCTAC GCACAAATCT TTACTGACTC TATCGCAGAA
CAAGGTAAAG AAGGCGACAG CTACTACAGC ATGATGAAAT
ACAACCTTGA CAAGATTGCT GAAGGATTGG CAAAATAAGC
CTCTGAAAAA CGTCATTCTC ATGTGAGCTG GCGTTTTTTC
TATGCCCACA TTTCCGGTCA AATCATTGGA AAATTCTGAC
TGTTTCAGAT ACAATGGAAG AAAAAGATT GGAGTATCCT
ATGGTAACTT TTCTCGGAAA TCCTGTGAGC TTTACAGGTA
AACAACTACA AGTCGGCGAC AAGGCGCTTG ATTTTTCTCT
TACTACAACA
```

179. (complement of psaA forward primer)
SEQ ID NO: 5

TCATTAGATCCTCCAATTTATTAGGGC 180. (complement of psaA reverse primer)
SEQ ID NO: 6

CGGAAAAAAAGATACAACTTCTGGTC 181. (complement of psaA probe)
SEQ ID NO: 7

TTTCTTTCTGCAATCATTCTTGTAGCATGTGCTAG 182. (2F Non-working fwd primer)
SEQ ID NO: 8

GCCCTAATAAATTGGAGGATCTAATGA 183. (2R Non-working fwd primer)
SEQ ID NO: 9

TTGACCAGAAGTTGTATCTTTTTTCC 184. (3F Non-working fwd primer)
SEQ ID NO: 10

CCCTAATAAATTGGAGGATCTAATGAAA 185. (3R Non-working fwd primer)
SEQ ID NO: 11

CAACTTTTAGTTTTGACCAGAAGTTGTA

---

What is claimed is:

1. An oligonucleotide primer for the amplification of a *Streptococcus pneumoniae* psa nucleic acid, wherein the oligonucleotide primer is 15 to 30 nucleotides in length and hybridizes, under conditions suitable for a polymerase chain reaction, with the nucleic acid sequence according to SEQ ID NO: 4, wherein the oligonucleotide primer comprises at least 15 consecutive nucleotides of the nucleic acid sequence according to SEQ ID NO: 1, and wherein the oligonucleotide primer is capable of directing the amplification of the *Streptococcus pneumoniae* psa nucleic acid.

2. A composition comprising the oligonucleotide primer of claim 1.

3. A kit comprising reagents for real-time PCR-type amplification reaction for detecting *Streptococcus pneumoniae*, comprising sense primers, antisense primers and a nondegenerate probe, wherein the sense primer is the oligonucleotide primer of claim 1.

4. An oligonucleotide primer for the amplification of a *Streptococcus pneumoniae* psaA nucleic acid, wherein the oligonucleotide primer is 15 to 30 nucleotides in length and hybridizes, under conditions suitable for a polymerase chain reaction, with the nucleic acid sequence according to SEQ ID NO: 4, wherein the oligonucleotide primer comprises at least 15 consecutive nucleotides of the nucleic acid sequence according to SEQ ID NO: 2, and wherein the oligonucleotide primer is capable of directing the amplification of the *Streptococcus pneumoniae* psaA nucleic acid.

5. A composition comprising the oligonucleotide primer of claim 4.

6. A kit comprising reagents for real-time PCR-type amplification reaction for detecting *Streptococcus pneumoniae*, comprising sense primers, antisense primers and a nondegenerate probe, wherein the antisense primer is the oligonucleotide primer of claim 4.

7. An oligonucleotide probe for the detection of a *Streptococcus pneumoniae* psa nucleic acid, wherein the oligonucleotide probe is 20 to 35 nucleotides in length and hybridizes, under conditions suitable for a polymerase chain reaction, with the nucleic acid sequence according to SEQ ID NO: 4 or the complement thereof, and wherein the oligonucleotide probe comprises at least 20 consecutive nucleotides of the nucleic acid sequence according to SEQ ID NO: 3 or SEQ ID NO: 7.

8. A composition comprising the oligonucleotide probe of claim 7.

9. The oligonucleotide probe of claim 7, wherein the oligonucleotide probe comprises the nucleotide sequence 5'-X-CTAGCACATGC "T"ACAAGAATGATTGCAGAAA-GAAA-Y-3' (SEQ ID NO: 3),
wherein X is a fluorophore,
wherein Y is a phosphate group or phosphate groups, and
wherein "T" is a thymine with a dark quencher or acceptor dye linked to it.

10. A kit comprising reagents for real-time PCR-type amplification reaction for detecting *Streptococcus pneumoniae*, comprising sense primers, and antisense primers and a nondegenerate probe, wherein the nondegenerate probe is the oligonucleotide probe of claim 7.

11. A kit comprising reagents for real-time PCR-type amplification reaction for detecting *Streptococcus pneumoniae*, comprising a sense primer, an antisense primer and a nondegenerate probe, wherein the sense primer is a nucleic acid molecule consisting of the nucleic acid sequence according to SEQ ID NO: 1;
the antisense primer is a nucleic acid molecule consisting of the nucleic acid sequence according to SEQ ID NO: 2; and
the non-degenerate probe is a nucleic acid molecule consisting of the nucleic acid sequence according to 5'-X-CTAGCACATGC"T"ACAAGAATGATTGCA-GAAAGAAA-Y-3' (SEQ ID NO: 3),
wherein X is a fluorophore,
wherein Y is a phosphate group or phosphate groups, and
wherein "T" is a thymine with a dark quencher or acceptor dye linked to it.

12. The oligonucleotide primer of claim 1, wherein the oligonucleotide primer is 25-30 nucleotides is length.

13. The oligonucleotide primer of claim 1, wherein the oligonucleotide primer hybridizes, under conditions suitable for a polymerase chain reaction, with the nucleic acid according to SEQ ID NO: 5.

14. The oligonucleotide primer of claim 1, wherein the oligonucleotide primer consists of a nucleic acid molecule with the nucleic acid sequence according to SEQ ID NO: 1.

15. The oligonucleotide primer of claim 4, wherein the oligonucleotide primer is 25-30 nucleotides is length.

16. The oligonucleotide primer of claim 4, wherein the oligonucleotide primer hybridizes, under conditions suitable for a polymerase chain reaction, with the nucleic acid according to SEQ ID NO: 6.

17. The oligonucleotide primer of claim 4, wherein the oligonucleotide primer consists of the nucleic acid sequence according to SEQ ID NO: 2.

18. The oligonucleotide primer of claim 7, wherein the oligonucleotide probe is 27-35 nucleotides is length.

19. The oligonucleotide probe of claim 7, wherein the oligonucleotide probe consists of the nucleotide sequence 5'-X-CTAGCACATGC "T"ACAAGAATGATTGCA-GAAAGAAA-Y-3' (SEQ ID NO: 3),
wherein X is a fluorophore,
wherein Y is a phosphate group or phosphate groups, and
wherein "T" is a thymine with a dark quencher or acceptor dye linked to it.

* * * * *